United States Patent [19]

Floyd, Jr.

[11] 4,260,805

[45] Apr. 7, 1981

[54] 1-DESCARBOXY-1-KETOESTER (KETOACID)-PROSTAGLANDINS

[75] Inventor: Middleton B. Floyd, Jr., Suffern, N.Y.

[73] Assignee: American Cyanamid Company, Stamford, Conn.

[21] Appl. No.: 79,621

[22] Filed: Sep. 27, 1979

[51] Int. Cl.³ .............................. C07C 177/00
[52] U.S. Cl. .................... 560/118; 260/408; 260/410.9 R; 260/413; 560/53; 560/121; 562/463; 562/500; 562/503; 424/305; 424/308; 424/317

[58] Field of Search ............... 560/121, 118; 562/503, 562/500; 260/408, 410.9 R, 413

[56] References Cited

U.S. PATENT DOCUMENTS 4,202,822  5/1980  Wissner .................. 542/429

Primary Examiner—Robert Gerstl
Attorney, Agent, or Firm—Richard J. Hammond

[57] ABSTRACT

This disclosure describes certain 11-hydroxy and 11-deoxy-1-ketocarboxylic acid prostanoic acids and derivatives useful as bronchodilators, hypotensive agents, anti-ulcer agents or intermediates.

59 Claims, No Drawings

1-DESCARBOXY-1-KETOESTER (KETOACID)-PROSTAGLANDINS

BACKGROUND OF THE INVENTION

1. Field of the Invention

The present invention relates to 15-deoxy-16-hydroxy-prostaglandins, as well as the pharmaceutically acceptable, non toxic lower alkyl esters and salts thereof, and to the intermediates and processes for producing such compounds.

2. Description of the Prior Art

Prostaglandins have classically been described as chemically related 20 carbon chain hydroxy fatty acids having the basic skeleton of prostanoic acid:

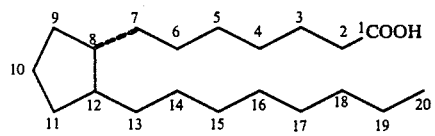

The prostaglandins having a hydroxyl group at the C-11 position and a keto group at the C-9 position are known as the PGE series, and those having a hydroxyl group in place of the keto group are known as the PGF series, and further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the PGF, and PGE, series refer to prostanoic acids having a trans-olefin bond at the C-13 position, while the $PGF_2$ and $PGE_2$ series refer to prostadienoic acids having a cis-olefin bond at the C-5 position and a trans-olefin bond at the C-13 position. For a review of prostaglandins and the definition of primary prostaglandins, see, for example, P. Ramwell, *The Prostaglandins*, 1, pp. 5–22 (1973).

The preparation of derivatives of prostanoic acid has become of great importance since the demonstration of the highly interesting range of biological and pharmacological activities of natural prostaglandins.

The great majority of these studies has focused on modification of the two side chains, or modifications of the substituents attached to the cyclopentane moiety (see for example, U. Axen et al., *Synthesis* Vol. 1, John Wiley and Sons Inc., New York, New York 1973 and P. H. Bently, *Chem. Soc.* Reviews 2, 29 (1973).

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Pat. No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeared (see for example, U.S. Pat. Nos. 3,950,006 and 4,132,738; and *Prostaglandins*, Vol. 10, 733 (1975).

Recently, reports have also appeared wherein the C-16 carbon bearing a hydroxyl group is substituted with a methyl group (see Pappo et al., *Tetrahedron Letters*, No. 4 235 (1975); Collin et al., U.S. Pat. No. 3,965,143; and Belgium Pat. No. 827,127.

Also, a patent has recently appeared wherein the C-16 carbon bearing the hydroxyl group is substituted with vinyl, methylvinyl, and cyclopropyl (U.S. Pat. No. 4,061,670).

SUMMARY OF THE INVENTION

In accordance with the present invention, we have prepared certain novel 15-hydroxy-prostaglandin analogs represented by the following formula:

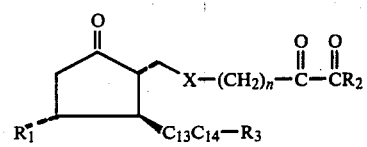

wherein $R_1$ is selected from the group hydrogen and hydroxy;

$R_2$ is selected from the group hydroxy and $C_1$ to $C_7$ alkoxy;

X is selected from the group cis or trans —CH=CH— and —CH$_2$—CH$_2$ $C_{13}C_{14}$ is selected from the group trans —CH=CH— and —CH$_2$—CH$_2$—;

n is the integer 2, 3 or 4; and $R_3$ is selected from the group consisting of:

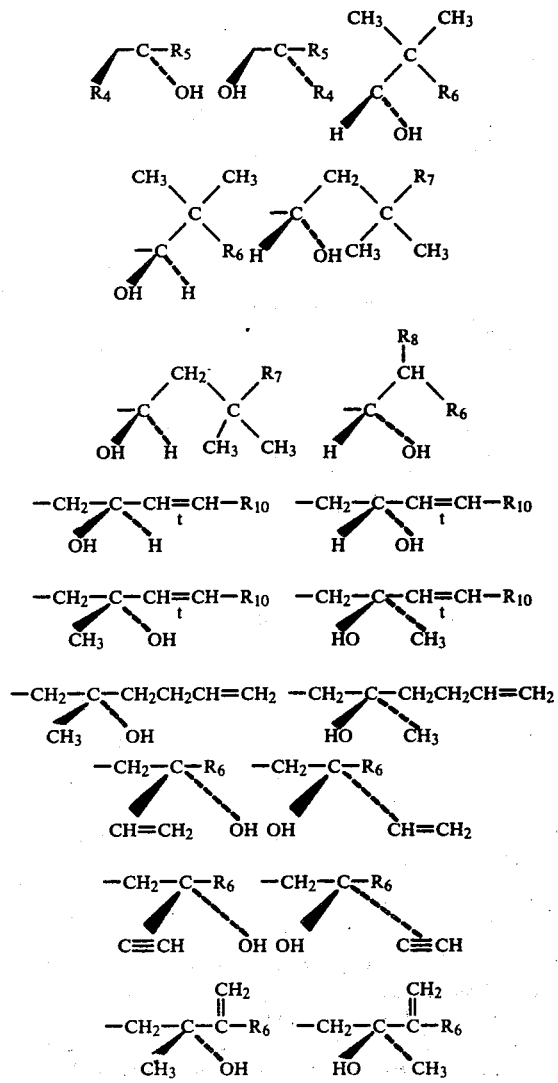

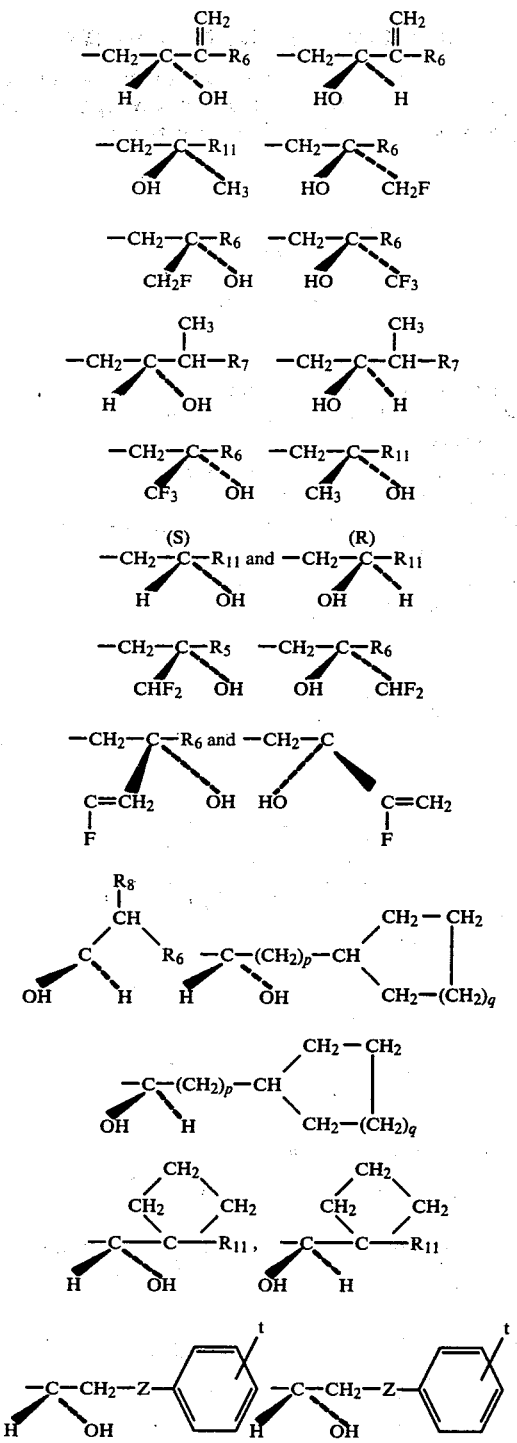

-continued wherein $R_4$ is hydrogen or methyl; $R_5$ is selected from the group consisting of $C_4$–$C_7$ alkyl; $R_6$ is selected from the group consisting of $C_3$–$C_5$ alkyl; $R_7$ is selected from the group consisting of $C_2$–$C_4$ alkyl; $R_8$ is selected from the group consisting of $C_1$–$C_2$ alkyl; $R_{10}$ is $C_1$ to $C_4$ alkyl $R_{11}$ is selected from the group consisting of $C_3$–$C_7$ alkyl; p is an integer from 0 to 3; q is 1 or 2; Z is a divalent radical selected from the group consisting of —O— or —$CH_2$—; and t is selected from the group consisting of hydrogen, chloro, fluoro, dichloro, trifluoromethyl, methoxy; the racemic mixtures thereof and, when $R_2$ is hydroxy, the pharmaceutically acceptable salts thereof.

The dotted lines shown in the above formula and in formulas below indicate that the substituents are in the α configuration, i.e., below the plane of the cyclopentane ring.

When a double bond appears at C-13 in some of the compounds of the present invention, these have the same configuration as the natural prostaglandins of the PGE series, that is, the trans configuration.

These novel compounds possess asymmetric centers and thus can be produced as racemic mixtures or as individual enantiometers. The racemic mixtures can be resolved if desired at appropriate stages by methods known to those skilled in the art, to obtain the respective individual enantiomers. It is to be understood that the racemic mixtures and the individual enantiomers are encompassed within the scope of the present invention.

When the compounds of the present invention are racemic mixtures, they are produced starting from racemates, while when the compounds of the invention are individual enantiomers the compounds are preferably obtained starting from the appropriate individual enantiomer.

Useful pharmacologically acceptable salts of the above formula, where $R_2$ is hydroxyl, are those with pharmacologically acceptable metal, ammonium, amine or quaternary ammonium cations.

Preferred metal cations are those derived from the alkali metals, e.g., lithium, sodium and potassium, and from the alkaline earth metals, e.g., magnesium and calcium, although cationic forms of other metals, e.g., aluminum, zinc and iron, are within the scope of this invention. Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and arylaliphatic amines containing up to and including 18 carbon atoms, as well as heterocyclic amines, e.g. piperidine, morpholine, pyrrolidine, paperazine and lower alkyl derivatives thereof, e.g. 1-methyl-piperidine, 4-ethylmorpholine, 1-isopropypyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

DESCRIPTION OF THE PREFERRED EMBODIMENTS

The compounds of the present invention comprise those of the formula

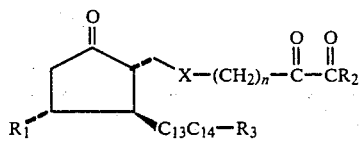

wherein
- $R_1$ is selected from the group hydrogen and hydroxy;
- $R_2$ is selected from the group hydroxy and $C_1$ to $C_7$ alkoxy;
- X is selected from the group cis or trans —CH=CH— and —CH$_2$—CH$_2$
- $C_{13}$-$C_{14}$ is selected from the group trans —CH=CH— and —CH$_2$—CH$_2$—;
- n is the integer 2, 3 or 4; and
- $R_3$ is selected from the group

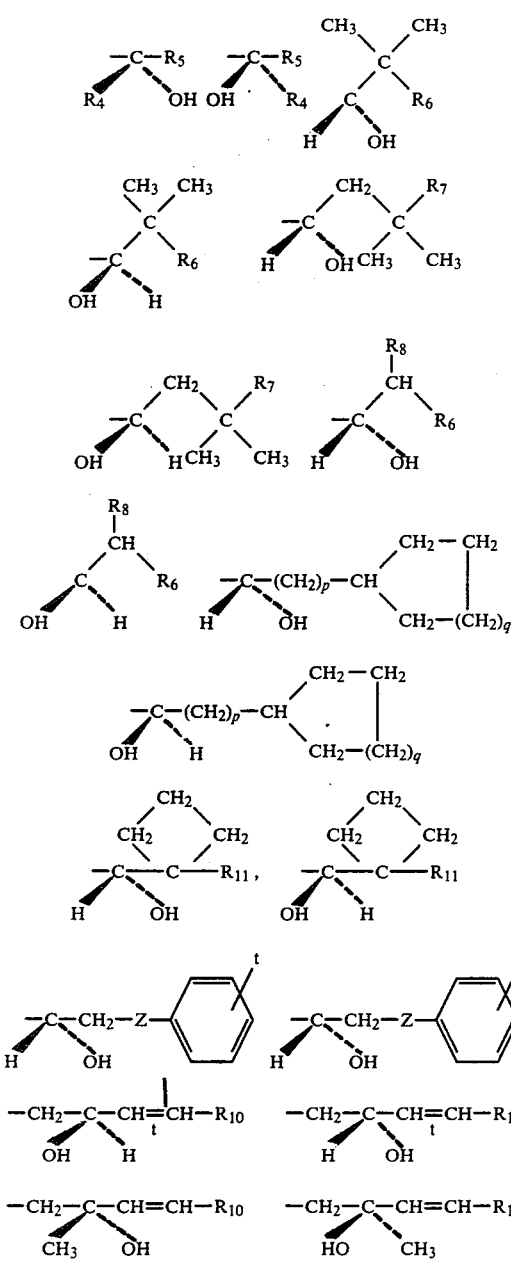

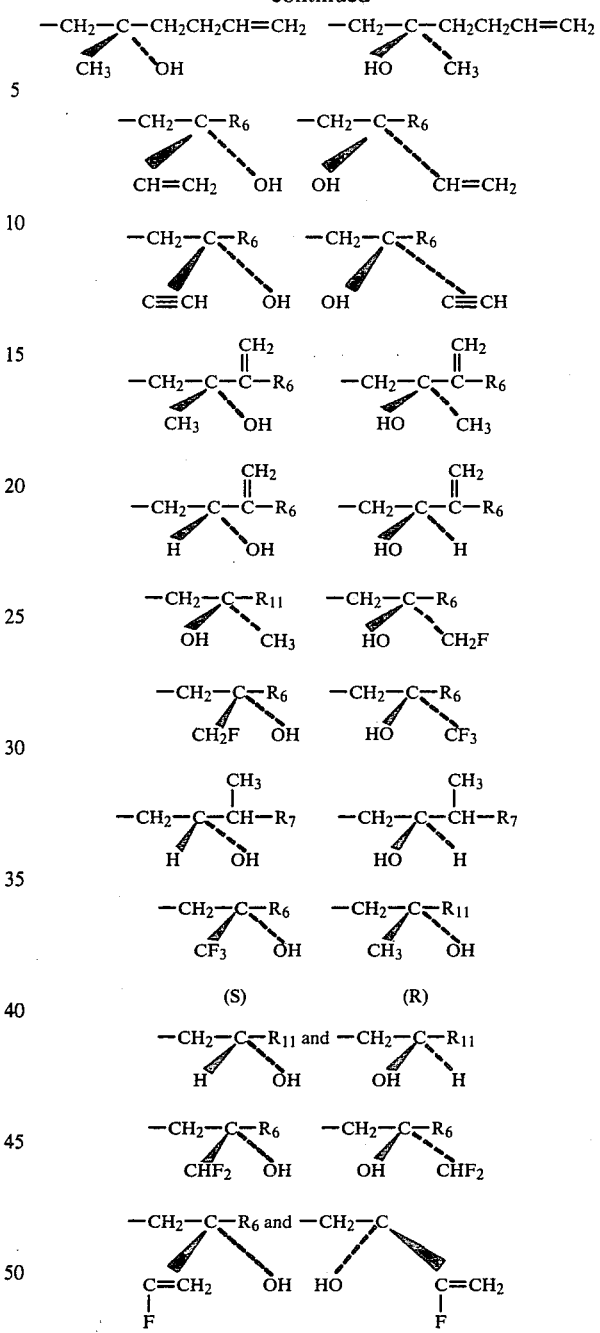

$R_4$ is hydrogen or methyl; $R_5$ is selected from the group consisting of $C_4$-$C_7$ alkyl; $R_6$ is selected from the group consisting of $C_3$-$C_5$ alkyl; $R_7$ is selected from the group consisting of $C_2$-$C_4$ alkyl; $R_8$ is selected from the group consisting of $C_1$-$C_2$ alkyl; $R_{10}$ is $C_1$ to $C_4$ alkyl $R_{11}$ is selected from the group group consisting of $C_3$-$C_7$; p is an integer from 0 to 3; q is 1 or 2;

Z is a divalent radical selected from the group consisting of —O— and —CH$_2$—; and t is selected from the group consisting of hydrogen, chloro, fluoro, dichloro, trifluoromethyl, methoxy, the racemic mixtures thereof, the mirror images thereof and, when $R_2$ is hydroxy, the pharmaceutically acceptable salts thereof.

The compounds of formula I are subgenerically represented by the following compounds:

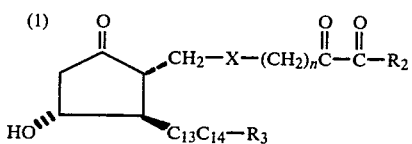
(1) Ia wherein X, $C_{13}C_{14}$, $R_2$, $R_3$ and n are as previously defined. In the compounds of formula Ia it is preferred that X is cis—CH=CH— or —CH$_2$—CH$_2$—, most preferably —CH$_2$—CH$_2$—; $R_2$ is ethoxy and $C_{13}C_{14}$ is trans —CH=CH—. In these preferred and most preferred compounds of formula Ia, it is preferred that $R_3$ is selected from the group

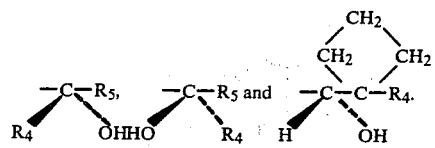

In these preferred and most preferred embodiments $R_1$, $R_4$, $R_5$, $R_6$, $R_8$, $R_{11}$, p, q, z and t are as previously defined.

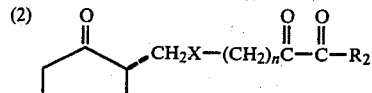
(2) Ib

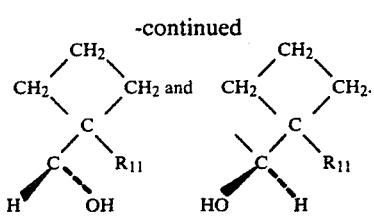

Most preferably R₃ is the moiety selected from the group

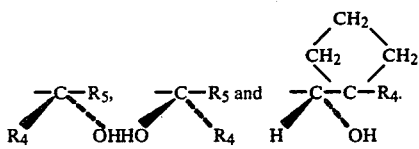

In these preferred and most preferred embodiments $R_1$, $R_4$, $R_5$, $R_6$, $R_8$, $R_{11}$, p, q, Z and t are as previously defined.

The novel compounds of this invention can be prepared by a 1,4-conjugate-addition procedure involving treatment of an ether blocked cyclopentenone of the formula

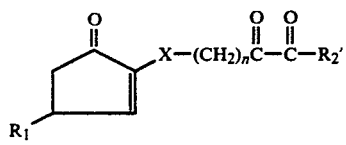

where X is as previously defined, $R_1'$ is hydrogen or n-trialkylsilyloxy, $R_2'$ is $C_1$ to $C_7$ alkoxy and n is an integer from 2 to 5, with a lithio-cuprate reagent of the formula

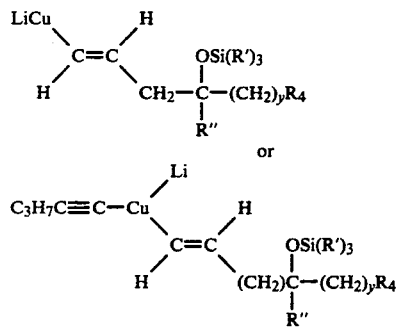

where R' is $C_1$ to $C_4$ alkyl, R" is $C_1$ to $C_4$ alkyl, hydrogen, $C_1$ to $C_4$ haloalkyl, $C_2$ to $C_4$ alkenyl, $C_2$ to $C_4$ alkynyl, optionally substituted aryl, etc., $R_4$ is hydrogen or $C_1$ to $C_4$ alkyl and y is an integer of from 0 to 4. The preparation reagents of this type are well known to those skilled in the art and is set forth in U.S. Pat. No. 4,061,670, issued Dec. 6, 1977 and U.S. Pat. No. 4,028,396, issued June 7 1977. These patents and patent applications are incorporated herein by reference. One method useful for the preparation of the lithio cuprate reagent IIa is the treatment of R" CHO where R" is as previously defined, with a propargylic magnesium halide to form the corresponding homopropargylic alcohol which is converted into the trialkylsilylether in the usual manner. The silylated derivative is then treated with disiamylborane, then trimethylamine oxide. The resulting solution and an iodine solution are added simultaneously to aqueous sodium hydroxide to give the 1-iodo-4-trialkylsilyloxytrans-1-alkene.

The trialkylsilyl protecting group is removed with mild acid and the resulting vinyl iodide alcohol is oxidized with pyridinium chlorochromate to provide the 1-iodo-4-oxo-trans-1-alkene, which upon treatment with the Grignard reagent $R_4(CH_2)_yMgX$, where $R_4$ and y are as previously defined, provides the 1-iodo-4-hydroxy-trans-1-alkene, which is silylated in the usual manner to provide the corresponding silyl ether. Reaction of the product of this reaction with n-butyllithium gives rise to the vinyl lithium compound IIc.

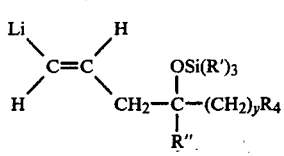

A more preferred method for the preparation of this vinyl lithium intermediate IIc is treatment of the R" carboxylic acid with the appropriate organolithium reagent to give the corresponding ketone, which upon treatment with propargylic magnesium halide provides the homopropargylic alcohol which is converted to the trans vinylstannyl derivative by sequential treatment with chlorotrimethylsilane and tri-n-butylstanyl hydride in the presence of azobisisobutrylnitrile. Treatment of the vnylstannyl reagent with n-butyllithium at a temperature of −10° to −78° C. generates the vinyllithium reagent IIc.

For the preparation of the asymmetrical lithio cuprate IIb a solution of one molar equivalent of a copper (I)-1-alkyne, preferably copper (I)-1-pentyne in anhydrous tributylphosphine or HMPTA, preferably one to five molar equivalents in either is added to one molar equivalent of the aforementioned vinyl lithium solution cooled to about −78° C. After about one hour at this temperature, a molar equivalent of a cyclopentenone is added. After several hours at −30° C. to −70° C. the reaction mixture is quenched with aqueous ammonium chloride solution and the blocked prostanoic acid is isolated in the usual manner.

It is also possible to effect conjugate 1,4-addition with an asymmetrical lithio cuprate derived from the vinyl lithium IIc and cuprous thiophenoxide. A solution of the vinyl lithium IIc in ether at −78° C. is reacted with an equimolar amount of a reagent prepared by admixture, in ether at a temperature of 0° C. to −78° C., of equimolar amounts of lithium thiophenoxide and copper (I) iodide-tributylphosphonium complex. After about 30 minutes at this temperature, the lithio cuprate is treated with a cyclopentenone as described hereinbelow for the conjugate addition with 1-alkynyl lithio cuprate.

For the preparation of the symmetrical lithio cuprate IIa one molar equivalent of copper (I) iodide tributylphosphine complex, dissolved in anhydrous ether, is added at about −78° C. to two molar equivalents of the aforementioned vinyl lithium IIa solution in hexane, or ether solvents cooled to −78° C. After about one hour at this temperature, the lithio cuprate IIa is treated with a cyclopentenone as described hereinbelow for the conjugate addition with the 1-alkynyl lithio cuprate.

The procedures for conjugate addition involving organocopper reagents are well known in the art, see for example C. J. Sih, et al., J. Amer, Chem. Soc., 97, 865 (1975) and the U.S. patents cited above.

In the cases where $R_1'$ is trimethylsilyloxy in the cyclopentenone, the conjugate addition is performed at −78° C. to −40° C. The reaction is quenched by addition of an ether solution of acetic acid. Removal of blocking groups is then carried out as described in the references above to provide the product prostanoic acid wherein $R_1$, $R_2$ and $R_3$ are as hereinabove defined.

In order to remove the trimethylsilyl protecting group from the C-15 or 16-hydroxyl of the compounds of the formula I bearing a pendent fluorinated alkyl group, more acidic conditions are required than for a non-fluorinated carbinol, therefor the addition of a small amount of hydrochloric acid is necessary.

The introduction of a racemic $\beta$-chain possessing the 15 or 16-hydroxy moiety provides a pair of prostaglandins epimeric at C-15 or 16. These two epimers may be separated into their upper (less polar) and lower (more polar) components by high-pressure liquid chromatography (HPLC) or by dry-column or preparative thin layer silica-gel chromatography.

If an optically active protected cyclopentenone is utilized, then HPLC separation will provide the corresponding optically active nat. 9-oxo-11α, 15α or 16α-dihydroxy-16-alkyl (or alkenyl, alkynyl, etc.) and nat. 9-oxo-11α, 15β or 16β-dihydroxy-16-alkyl (or alkenyl, alkynyl, etc.) —PGE enantiomers as well as, when $R_1$=hydrogen, the corresponding 11-deoxy-PGE enantiomers.

For the preparation of the intermediate cyclopentenones required to prepare the compounds of formula I, three procedures are necessary depending on whether (a) the α-chain is intended to have unsaturation at the 5-position, (b) the α-chain is to be fully saturated, or (c) the product compound is to be of the 11-deoxy series (unsaturated or saturated α-chain).

Procedure (a): In accordance with Flowsheet A, reaction of a 2-(ω-carboalkoxyalkene)-2,5-dialkoxy dihydrofuran 1 with a dialkyl oxalate in an alkali or alkaline earth metal hydride-catalyzed solution or suspension results in addition of an alkoxyoxalyl group at the α-carbon of the ω-carboalkoxyalkene side chain to provide 2. Treatment of 2 with a solution of a weak acid, preferably phosphate buffer, in an inert organic solvent such as aqueous dioxane converts the dihydrofuran ring to the 3-hydroxycyclopent-4-en-1-one 3. Treatment of the reaction solution of 3 with sulfuric acid, followed by heating, simultaneously results in hydrolysis of the ester groups, decarboxylation and rearrangement of the 3-hydroxycyclopent-4-en-1-one to the 4-hydroxycyclopent-2-en-1-one 4 bearing, at the 2-position, the ω-carboxylic acid side chain with an α-carbon keto group. After esterification of the carboxylic acid group in the conventional manner in an alcohol solution containing a catalytic amount of mineral acid such as sulfuric acid, the α-ketoester intermediate 5 is treated with one equivalent of 1,1-dimethylhydrazine to provide selectively the mono-dimethylhydrazone derivative 6. The hydroxy group in 6 is blocked with a suitable protecting group, for example the group trimethylsilyl, to provide the cyclopentenone 7 required for conjugate addition, where P is a suitable protecting group, such as trimethylsilyl.

Procedure (b): In those compounds of formula I where the α-chain is intended to be saturated and $R_1$ is intended to be hydroxy, the requisite cyclopentenone is prepared in accordance with Flowsheet B. A (2-furyl-)(ω-carboalkoxyalkyl)carbinol 1 is reacted with a dialkyl oxalate as described above for the preparation of 2, Flowsheet A. The intermediate 2 is treated in aqueous dioxane with a moderately strong acid, for example formic acid or a mixture of phosphoric acid and sodium dihydrogen phosphate to convert the furylcarbinol moiety to a 3-hydroxycyclopent-4-en-1-one moiety and simultaneously to effect hydrolysis of the ester groups and decarboxylation, thereby providing 3. Addition of stronger acid, for example sulfuric acid, followed by heating results in rearrangement of the 3-hydroxycyclopent-4-en-1-one to the 4-hydroxycyclopent-2-en-1-one 4. The remaining steps are carried out as in Flowsheet A, namely esterification to provide the α-ketoester 5, formation of the mono-dimethylhydrazone derivative 6, and protection of the free hydroxy group of 6 with a suitable group to give 7, where P is a blocking group, for example trimethylsilyl.

Procedure (c): In these compounds of formula I where $R_1$ is intended to be hydrogen, a preferred technique for synthesis of the cyclopentenone intermediates is set forth in Flowsheet C. A 2-(ω-carboalkoxyalkyl)-cyclopent-2-en-1-one 1 is treated with an alkoxyamine, preferably methoxyamine, to form the corresponding methoxime 2. Treatment of 2 with a dialkyl oxalate as described above in Flowsheets A and B provides the corresponding -alkoxyoxalyl ester 3. Treatment of 3 with strong acid, for example hydrochloric acid, in a mixed solvent, preferably aqueous acetone, results in hydrolysis of the ester groups accompanied by decarboxylation and hydrolysis of the methoxime function to provide 4. Esterification of 4 in the conventional manner provides 5 and treatment of the latter with 1,1-dimethylhydrazine selectively provides the requisite cyclopenenone 6.

The prostaglandin carboxylic acids of this invention can be readily converted to the various alkyl esters of this invention by treatment in the usual manner with the appropriate diazolalkane. The preparation of diazoalkanes by various procedures are well described in the art. See for example C. D. Gutsche, *Organic Reactions,* VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a trialkylamine, preferably triethylamine, tributylamine and the like, and then a molar equivalent of isobutyl chlorocarbonate or the like. The resulting mixed anhydrides are then treated with the appropriate alcohol to give the derivatized product. (For a pertinent literature analogy see *Prostaglandins,* 4, 768 (1973).

An alternative procedure involves treatment of the prostaglandin acid with a molar equivalent of the trialkyl amine in an excess of the appropriate alcohol and an anhydrous solvent such as methylene chloride. A molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279).

A third procedure for conversion of the carboxylic acids to the corresponding esters involves the use of dicyclohexylcarbodiimide in the usual manner; for a pertinent literature analogy see German Offen. 2,365,205; Chem. Abst., 81, 120098g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. (See G. Fallick, American Laboratory, 19–27 (August 1973) as well as references cited therein. Additional information concerning high speed liquid chromatography and the instruments necessary for its application is available from Waters Associates Inc., Maple St., Milford, Mass.).

The following examples are illustrative of the preferred embodiments of this invention, but are not meant to limit it in any way. A variety of modifications and variations will become obvious to those skilled in the art upon a reading of the present application, and all such obvious variations and modifications are to be taken as being within the scope of the claims appended hereto. Unless indicated to the contrary, all temperatures are in degrees centigrade.

PREPARATION 1

31.9 g of 502. sodium hydride in oil is washed free of mineral oil with light petroleum, suspended in 125 ml of ether, cooled to 0°, and treated with 19.4 ml of absolute ethanol. To the stirred mixture is added a solution of 84.4 g of 6-carbethoxyhexyl(2-furyl)carbinol and 60.7 g of diethyl oxalate during 30 minutes at 0°–10°. The resulting mixture is stirred at room temperature for 18 hours and at reflux temperature for 2 hours. The cooled mixture is diluted with ether cooled to 0°, and treated with 400 ml of 2 N HCl. The ether phase is washed with water and brine, dried over magnesium sulfate, and concentrated to give an oil (100 g) 6-carbethoxy-6-ethoxyoxalylhexyl-(2-furyl)carbinol.

PREPARATION 2

To a stirred mixture of 100 g of crude 6-carbethoxyethoxyoxalylhexyl(2-furyl)carbinol (Preparation 1) 23.6 g of sodium bicarbonate, 1.5 g of hydroquinone, 1650 ml of dioxane, and 1240 ml of water is slowly added 250 ml of 90% formic acid. The solution which results on heating is maintained at reflux temperature for 22 hours.

To the above solution at 50°–60° is added 75 ml of conc sulfuric acid during 15 minutes, and the resulting solution is heated under reflux for 18 hours. The solution is cooled, diluted with ethyl acetate, and saturated with sodium chloride. The ethyl acetate phase is washed with brine, dried over magnesium sulfate and concentrated.

The residue (100 g) is dissolved in 2640 ml of ethanol and 825 ml of tolene with 5.9 g of p-toluenesulfonic acid, and the resulting solution is boiled for 4 hours during which time 900 ml of distillate is collected. The solution is concentrated and diluted with ethyl acetate. The solution is washed with sodium bicarbonate solution and brine, dried over magnesium sulfate, and concentrated.

The crude product is subjected to chromatography on silica gel with ethyl acetate in hexane as developing solvent to provide a light amber oil (27.5 g) 2-(7-carbethoxy-7-oxo-heptyl)-4-hydroxycyclopent-2-en-1-one.

PREPARATION 3

To a stirred solution of 25.6 g of 2-(7-carbethoxy-7-oxoheptyl)-4-hydroxycyclopent-2-en-1-one (Preparation 2) and 5.55 ml of gl acetic acid in 270 ml of toluene is added dropwise a solution of 5.56 g of N,N-dimethylhydrazine in 90 ml of toluene during 5 minutes. After 45 minutes at room temperature the solution is evaporated to give a reddish oil (29.4 g) 2-7-carbethoxy-7-(2,2-dimethylhydrazona)-heptyl-4-hydroxycyclopent-2-en-1-one.

PREPARATION 4

To a stirred suspension of 29.4 g of 2-7-carbethoxy-7-(2,2-dimethylhydrazona)-heptyl-4-hydroxycyclopent-2-en-1-one (Preparation 3) in 360 ml of petroleum ether is added 22.4 ml of N,N-bis(trimethylsilyl)acetamide during 10 minutes. After 1.5 hours the mixture is cooled to 0° and filtered. The filtrate is subjected to evaporation of volatile material in vacuo (0.1 mm, 65°) to provide a reddish liquid (35.2 g) 2-[7-carbethoxy-7-(2,2-dimethylhydrazona)-heptyl-4-trimethylsilyloxy-cyclopent-2-en-1-one.

PREPARATION 5

A solution comprised of 79.5 g. of 5-oxo-1-cyclopentene-1-heptanoic acid, ethyl ester, 33.4 g. of methoxyamine hydrochloride, 55 ml- of pyridine and 650 ml. of absolute ethanol is allowed to stand under nitrogen for 24 hours. The bulk of the ethanol is evaporated at reduced pressure. The residue id partitioned between 600 ml. of ether and 200 ml. of 50% saturated sodium chloride solution. The ether phase is washed with 100 ml. of 50% saturated sodium chloride solution, then three 100 ml. portions of saturated sodium chloride solution, dried over magnesium sulfate and evaporated. The residue is subjected to Kugelrohr distillation giving 83.8 g. of a light yellow liquid 2-(6-carbethoxyhexyl)-cyclopent-2-en-1-one methoxime.

PREPARATION 6

A stirred suspension of 13.0 g. of sodium methoxide in 100 ml. of toluene is treated successively with 94.5 g. of dimethyl oxalate and a solution of 48.0 g. of 2-(6-carbethoxyhexyl)-cyclopent-2-en-1-one methoxime in 60 ml. of toluene. The flask is arranged for vacuum distillation and is equipped with a thermometer, taking care to exclude air. The contents are maintained at 65° C., while slowly distilling out liquid (aspirator; 150–25 mm. mercury). After 5 hours most of the toluene has been removed. The residue is cooled, diluted with 400 ml. of ether, treated with 22 ml. of glacial acetic acid and the resulting slurry is added to 200 ml. of 1 N hydrochloric acid. The aqueous phase is re-extracted with 200 ml. of ether. The ether phases are combined, washed with two 150 ml. portions of water, then three 150 ml. portions of brine, dried over magnesium sulfate and evaporated to give an amber liquid. 2-(6-carbomethoxy-7-oxo-7-carbomethoxy-heptyl)-cyclopent-2-en-1-one methoxime.

PREPARATION 7

A stirred solution of 70 g. of 2-(6-carbomethoxy-7-oxo-7-carbomethoxyheptyl)-cyclopent-2-en-1-one methoxime in 720 ml. of acetone and 360 ml. of 4 N hydrochloric acid is refluxed under nitrogen for 26 hours. The solution is cooled, saturated with solid sodium chloride and extracted with three 400 ml. portions of ether. The ether extracts are combined, washed with four 200 ml. portions of brine, dried over magnesium sulfate and evaporated to about 400 ml. The concentrate is diluted with benzene, evaporated to remove water, then diluted with ether and filtered. The filtrate is evaporated giving a dark viscous oil. 2-(7-oxo-7-carboxyheptyl)-cyclopent-2-en-1-one.

PREPARATION 8

A stirred solution of 53 g. of 2-(7-oxo-7-carboxyheptyl)-cyclopent-2-en-1-one, 0.90 g. of p-toluenesulfonic acid monohydrate, 300 ml. of absolute ethanol and 300 ml. of benzene is heated to reflux temperature during 15 minutes under nitrogen. After 30 minutes at reflux, 25 ml. of distillate is distilled out of solution during 10 minutes. Reflux is continued for 30 minutes and an additional 25 ml. of distillate is removed. This is repeated six times removing a total of 150 ml. of distillate over a period of 4 hours. The solution is concentrated at reduced pressure to 150 ml., diluted with 500 ml. of ether and washed successively with 100 ml. of brine, two 50 ml. portions of saturated sodium bicarbonate solution and three 100 ml. portions of brine and dried over magnesium sulfate. Evaporation gives 31.5 g. of reddish liquid. A 1.6 g. portion of this liquid is suspended in 5 ml. of hexane:ether (10:1) and developed on a column of 70 g. of silica gel, wet packed in hexane:ether (10:1), 2.0×28 cm., eluting as follows:

| Fractions | Volume | Solvent | |
|---|---|---|---|
| 1 | 250 ml. | Hexane:ether | (10:1) |
| 2 | 200 | " | " |
| 3 | 50 | " | (8:1) |
| 4,5 | 250 | " | " |
| 6 | 250 | " | (7:1) |
| 7–10 | 250 | " | (6:1) |
| 11,12 | 250 | " | (5:1) |
| 13–16 | 250 | " | (4:1) |
| 17,18 | 250 | " | (3:1) |
| 19 | 200 | " | " |
| 20 | 150 | " | " |
| 21–33 | 100 | " | " |
| 34,35 | 100 | " | (5:2) |
| 36 | 300 | " | (2:1) |

Fractions 23–31 are combined giving 0.28 g. of a light yellow liquid. Fractions 32–36 and 22 are combined giving 0.14 g. 2-(7-Oxo-7-carbethoxyheptyl)-cyclopent-2-en-1-one a light yellow liquid. Total yield 0.42 g. of the desired product.

PREPARATION 9

To a stirred solution of 0.14 g. of 2-(7-oxo-7-carbethoxyheptyl)-cyclopent-2-en-1-one in 2.5 ml. of absolute ethanol under nitrogen is added 1.0 ml. of a 0.5 M. solution of unsymetrical dimethylhydrazine in absolute ethanol. The solution is stirred overnight, diluted with 20 ml. of benzene and evaporated giving 0.15 g. 2-[7-(2,2′-Dimethylhydrazinyl)-7-carbethoxyheptyl]cyclopent-2-en-1-one as a yellow oil.

PREPARATION 10

To a stirred suspension of 16.8 g. of a 50% sodium hydride in oil dispersion and 50 ml. of ether is added a solution of 49.7 g. of 2-(7-carbomethoxy-3-cis-heptenyl)-2,5-dimethoxy-2,5-dihydrofuran and 28.2 g. of diethyl oxalate in 100 ml. of ether, during one hour. The mixture is stirred for one hour and then at reflux (40° C.) for 1.5 hours, then allowed to stand overnight. The mixture is stirred at 0° to 5° C., while 10 ml. of ethanol is added slowly during 30 minutes. The mixture is stirred at room temperature for one hour, then at reflux (35°–40° C.) for 3.5 hours. The dark solution is cooled to 0° C. and treated cautiously with 700 ml. of ice water. The mixture is extracted with three 300 ml. portions of ether:petroleum ether (1:1). The aqueous phase is separated, cooled to 0° C., stirred with 300 ml. of ethyl acetate and treated with 33 ml. of glacial acetic acid. The mixture is further acidified to pH 4 with 200 ml. of 1 N hydrochloric acid at 0° C., quickly extracted with three 300 ml. portions of ethyl acetate and the combined extracts are immediately washed with 50 ml. portions of saturated sodium bicarbonate solution until the pH is 8–9. The extracts are then washed with four 75 ml. portions of brine, dried over magnesium sulfate and evaporated giving 2-(7-Carbethoxy-8-oxo-8-carbethoxy-3-cis-octenyl)-2,5-dimethoxy-2,5-dihydrofuran as an amber liquid.

PREPARATION 11

To a stirred solution of 20.7 g. of 2-(7-carbethoxy-8-oxo-8-carbethoxy-3-cis-octenyl)-2,5-dimethoxy-2,5-dihydrofuran and 100 mg. of hydroquinone in 210 ml. of dioxane is added a solution of 16.8 g. of disodium phosphate heptahydrate and 17.3 g. of monosodium phosphate monohydrate in 470 ml. of water. This mixture is refluxed for 2 hours, then cooled to 70° C. and treated dropwise with 19 ml. of concentrated sulfuric acid during 10 minutes. The mixture is stirred at reflux for 20 hours, cooled, saturated with solid sodium chloride and extracted with four 200 ml. portions of ethyl acetate. The combined extracts are washed with four 100 ml. portions of brine, dried over magnesium sulfate and evaporated giving 2-(7-Oxo-7-carboxy-2-cis-heptenyl)-4-hydroxycyclopent-2-en-1-one the desired product (16.3 g.) as a dark oil.

PREPARATION 12

A stirred solution of 16.3 g. of 2-(7-oxo-7-carboxy-2-cis-heptenyl)-4-hydroxycyclopent-2-en-1-one, 50 ml. of absolute ethanol, 0.96 g. of p-toluenesulfonic acid and 150 ml. of toluene is heated at reflux. After one hour, 75 ml. of distillate is collected. After 4 hours, another 75 ml. of distillate is collected. Reflux is continued an additional 30 minutes, then most of the ethanol is evaporated at reduced pressure and the residue is dissolved in 300 ml. of ethyl acetate. This solution is washed successively with 150 ml. of half-saturated brine, two 50 ml. portions of brine, 0.1 M. sodium bicarbonate (1:1) and three 50 ml. portions of brine, dried over magnesium sulfate and evaporated to a dark oil. This oil is dissolved in 30 ml. of ethyl acetate:hexane (3:1) and the solution is developed on a dry column of 750 g. of silica gel (3.2×146 cm.), pre-equilibrated with 75 ml. of the same solvent. The column is eluted with the same solvent, allowing 200 ml. to exit. The fractions are segmented as follows and eluted with ethyl acetate.

| Fraction | cm. from top |
|---|---|
| 1 | 67–70 |
| 2 | 73 |
| 3 | 76 |
| 4 | 79 |
| 5 | 82 |
| 6 | 85 |
| 7 | 88 |
| 8 | 91 |
| 9 | 94 |
| 10 | 97 |

Fractions 3–8 are combined giving 2.28 g. of 2-(7-Oxo-7-carbethoxy-2-cis-heptenyl)-cyclopent-2-en-1-one as an amber liquid.

PREPARATION 13

To a stirred solution of 2.07 g. of 2-(7-oxo-7-carbethoxy-2-cis-heptenyl)-cyclopent-2-en-1-one in 15 ml. of pyridine at 0° C. is successively added 2.1 ml. of hexamethyldisilazane and 1.1 ml. of chlorotrimethylsilane. The mixture is stirred for 4 hours and the volatile matter is removed under high vacuum at 40° C. The residue is stirred with 100 ml. of petroleum ether, filtered through Celite and concentrated giving 2.37 g. of 2-(7-Oxo-7-carbethoxy-2-cis-heptenyl)-4-trimethylsilyloxycyclopent-2-en-1-one as a reddish liquid.

PREPARATION 14

2-[7-(2',2'-Dimethylhydrazinyl)-7-carbethoxy-2-cis-heptenyl]-4-trimethylsilyloxycyclopent-2-en-1-one To a stirred solution of 2.37 g. of 2-(7oxo-7-carbethoxy-2-cis-heptenyl)-4-trimethylsilyloxycyclopent-2-en-1-one in 20 ml. of dry toluene, under nitrogen, is added 15 ml. of 0.5 M. dimethylhydrazine in toluene, via a syringe during 2 minutes. The solution is stirred for one hour, 0.45 ml. of glacial acetic acid is added and stirring is continued for 2 more hours. The mixture is evaporated to dryness, 25 ml. of toluene is added and the mixture is evaporated twice giving 2.42 g. of an amber viscous liquid which is the desired product and the unsilylated hydrazone in a 2:3 ratio. This liquid is suspended in 10 ml. of dry petroleum ether and one ml. of bis(trimethylsilyl)acetamide is added via a syringe. The mixture is stirred for 30 minutes, diluted with 25 ml. of toluene and evaporated. The toluene addition and evaporation are repeated twice giving a residue of an amber oil. This oil is slurried with 25 ml. of dry petroleum ether and filtered. The filtrate is evaporated giving 2.29 g. of the desired product as an amber oil.

EXAMPLE 1 dl-1-Carbethoxy-1,9-dioxo-15(RS)-hydroxy-15-methyl-13-trans prostene

To a stirred solution of 7.16 g. of 1-iodo-3-methyl-3-trimethylsilyloxy-trans-1-octene in 42 ml. of ether at −78° C. is added 26.2 ml. of a 1.6 M. solution of t-butyllithium in pentane over 10 minutes. The temperature is raised to −10° C. during 30 minutes, and the mixture is stirred at −10° C. for one hour, then at zero to −5° C. for 10 minutes and recooled to −78° C.

To a 2.7 g. portion of pentynyl copper is added 9.0 ml. of hexamethyl phosphorous triamide. The mixture is stirred vigorously for 30 minutes, diluted with 70 ml. of ether, cooled to −50° C. and added, over 10 minutes, to the above vinyllithium solution. The solution is stirred at −78° C. for 45 minutes and then treated during 10 minutes with a solution of 4.46 g. of 2-[7-(2,2'-dimethylhydrazinyl)-7-carbethoxyheptyl]cyclopent-2-en-1-one (Preparation 9) in 25 ml. of ether. The mixture is stirred at −78° C. for 5 minutes, then at −25° C. for 30 minutes, then at −25° to −20° C. for 90 minutes, recooled to −78° C. and quenched with 2.6 ml. of glacial acetic acid in 30 ml. of ether. The mixture is diluted to 400 ml. with ether and poured into a stirred mixture of 120 ml. of ice cold saturated ammonium chloride solution and 170 ml. of 1 N hydrochloric acid. The mixture is stirred vigorously at 0° C. for 5 minutes, filtered through Celite and the ether phase is washed successively with two 75 ml. portions of brine, dried over magnesium sulfate and evaporated to a light amber liquid. This liquid is dissolved in a mixture of 120 ml. of glacial acetic acid, 60 ml. of tetrahydrofuran and 30 ml. of water. This mixture is stirred for 1.5 hours, diluted with 220 ml. of half-saturated brine and extracted with three 150 ml. portions of ether. The extracts are washed with 150 ml. of half-saturated brine, then six 50 ml. portions of saturated brine, dried over magnesium sulfate and evaporated to a light amber oil. This oil is dissolved in 10 ml. of toluene-:ethyl acetate (3:1) and developed on a dry column of 750 g. of silica gel, pre-equilibrated with 50 ml. of the same solvent, 3.2×148 cm., eluted to the end of the column with the same solvent and allowing 375 ml. to exit. The fractions are segmented as follows:

| Fraction | cm. from top |
|---|---|
| 1 | 68–70.5 |
| 2 | 73 |
| 3 | |
| 4 | 78 |
| 5 | |
| 6 | 83 |
| 7 | |
| 8 | 88 |
| 9 | |
| 10 | 93 |
| 11 | |
| 12 | 98 |
| 13 | |
| 14 | 103 |
| 15 | |
| 16 | 108 |
| 17 | |
| 18 | 113 |
| 19 | |
| 20 | 118 |

Fractions 5–17 are combined to give 2.74 g. of the captioned product after elution with ethyl acetate.

EXAMPLE 2 dl-1,9-Dioxo-1-carbethoxy-11α,16-dihydroxy-16-methyl-5-cis-13-trans-prostadiene

A solution of 2.52 g. of E-1-tri-n-butylstannyl-4-methyl-4-trimethylsilyloxy-1-octene in 4 ml. of tetrahydrofuran is subjected to exchange reaction with 2.0 ml. of 2 M. n-butyllithium.

A solution of 0.58 g. of pentynylcopper and 1.6 ml. of hexamethyl phosphorous triamide in 10 ml. of ether is cooled to −78° C. and added during 5 minutes to the stirred vinyllithium solution at −75° C. The resulting solution is stirred at −78° C. for one hour and then treated with a solution of 0.79 g. of 2-[7-(2',2'-dimethylhydrazinyl)-7-carbethoxy-2-cis-heptenyl]-4-trimethylsilyloxycyclopent-2-en-1-one (Preparation 4 or 14) in 5 ml. of either during 5 minutes. The resulting solution is warmed to −40° C., held at −40° C. for 1.5 hours, recooled at −78° C. and quenched with a solution of 0.5 ml. of glacial acetic acid in 10 ml. of ether. The solution is diluted to 75 ml. with ether and poured into a stirred 0° C. mixture of 20 ml. of saturated ammonium chloride and 20 ml. of 1 N hydrochloric acid. The mixture is stirred 5 minutes and the phases are separated. The aqueous phase is extracted with 25 ml. of ether. The ether phases are combined, washed successively with two 10 ml. portions of 2 N hydrochloric acid at 0° C., three 15 ml. portions of water and three 15 ml. portions of brine, dried over magnesium sulfate and evaporated giving 3.14 g. of a mixture of a colorless liquid and an amber oil. A 3.1 g. portion of this mixture is dissolved in 30 ml. of ethanol, treated with 10 ml. of glacial acetic acid, allowed to stand for 4 hours, heated at 40° C. for one hour and the solvents are evaporated at 30° C. under high vacuum giving a mixture of a colorless liquid and an amber oil. This mixture is stirred with 20 ml. of heptane, transferred to 15 g. of silica gel on a sintered funnel and washed with 150 ml. of heptane. The heptane insoluble portion is washed through with 200 ml. of ethyl acetate which is then evaporated giving 1.20 g. of a mixture of solid and amber oil. This mixture is dissolved in 4 ml. of ethyl acetate:heptane (3:1) and developed on a 1.9×118 cm. dry column of 200 g. of silica gel pre-equilibrated with 20 ml. of the same solvent. The column is eluted to the end with the same solvent and then 100 ml. is allowed to exit. Fractions are segmented as follows and then eluted with 5% ethanol in ethyl acetate.

| Fraction | cm. from top |
| --- | --- |
| 1 | 52–54 |
| 2 | 56 |
| 3 | 58 |
| 4 | 60 |
| 5 | 62 |
| 6 | 64 |
| 7 | 66 |
| 8 | 68 |
| 9 | 70 |
| 10 | 72 |
| 11 | 74 |
| 12 | 76 |
| 13 | 78 |
| 14 | 80 |

Fractions 5–12 are pooled giving the captioned product.

EXAMPLE 3 dl-1,9-Dioxo-1-carbethoxy-11α,16-dihydroxy-16-vinyl-5-cis-13-trans-prostadiene

A solution of 2.07 g. of E-1-tri-n-butylstannyl-4-trimethylsilyloxy-4-vinyl-1-octene in 3.2 ml. of tetrahydrofuran is treated with 1.3 ml. of 2.5 M. n-butyllithium in hexane at −78° C. The exchange reaction is carried out at −40° C. for 90 minutes and −30° C. for 10 minutes. The cuprate reagent is prepared as described in Example 2, from the above vinyllithium solution, 0.46 g. of pentynyl copper, 1.3 ml. of hexamethylphosphorous triamide and 8 ml. of ether. To the stirred mixture is added at −78° C. 0.64 g. of 2-[7-(2′,2′-dimethylhydrazinyl)-7-carbethoxy-2-cis-heptenyl]-4-trimethylsilyloxycyclopent-2-en-1-one (Preparation 4 or 14) in 4 ml. of ether. The reaction is carried out at −40° C. for 90 minutes. recooled to −78° C. and quenched with a solution of 0.4 ml. of glacial acetic acid in 10 ml. of ether. The solution is diluted to 75 ml. with ether and poured into a stirred mixture of 20 ml. of saturated ammonium chloride and 20 ml. of 1 N hydrochloric acid at 0° C. The mixture is stirred vigorously at 0° C. for 5 minutes. The ether phase is separated and washed successively with two 20 ml. portions of 1 N hydrochloric acid, two 20 ml. portions of water, 10 ml. of half-saturated sodium bicarbonate, all at 0° C., and two 20 ml. portions of brine, dried over magnesium sulfate and evaporated to a mixture of an amber oil and a liquid. This mixture is dissolved in 16 ml. of absolute ethanol and treated with 8 ml. of glacial acetic acid. The solution is allowed to stand for 4 hours, heated at 40° C. for 30 minutes, toluene is added and the mixture is evaporated at 30° C. The residue is dissolved in 25 ml. of heptane and passed through a silica column as described in Examples 1 and 2. The ethyl acetate fraction is evaporated to an amber oil. This oil is dissolved in 16 ml. of ethanol and 8 ml. of acetic acid, stirred at 40° C. for one hour and the solvents are evaporated. The residue is dissolved in 3 ml. of ethyl acetate:heptane (3.1) and chromatographed as described in Examples 1 or 2 to give the captioned product.

By using the procedures of Example 1, the following vinyl tin or vinyl iodide intermediates are treated with the illustrated cyclopentenone to form the exemplified 15-hydroxy prostaglandins of the E-series.

| EXAMPLE | VINYL IODIDE | CYCLOPENTENONE | PRODUCT PROSTAGLANDIN OF THE 11-DEOXY PGE2 SERIES |
|---|---|---|---|
| 4 | 1-trans-iodo-4-triphenylmethoxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-20-nor-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 5 | 1-trans-tri-n-butylstannyl-4-methyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-20-nor-2-nor-5-cis-13-trans prostadiene |
| 6 | 1-trans-tri-n-butylstannyl-4-ethyl-4-trimethylsilyloxy-1-octene | 2-[6-carbethoxy-6-(2,2-dimethylhydrazono)hex-2-cis-enyl]cyclopent-2-en-1-one | dl-16-hydroxy-1-carbethoxy-1,9-dioxo-16-ethyl-2-nor-cis-13-trans prostadiene |
| 7 | 1-trans-tri-n-butylstannyl-5-methyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-17-methyl-20-nor-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 8 | 1-trans-iodo-5,5-dimethyl-4-trimethylsilyloxy-1-octene | 2-[6-carbethoxy-6-(2,2-dimethylhydrazono)hex-2-cis-enyl]cyclopent-2-en-1-one | dl-16-hydroxy-1-carbethoxy-1,9-dioxo-17,17-dimethyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 9 | 1-trans-tri-n-butylstannyl-4-vinyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-vinyl-20-nor-2-nor-5-cis-13-trans prostadiene |
| 10 | 1-trans-tri-n-butylstannyl-4-cyclopropyl-4-trimethylsilyloxy-1-octene | 2-[6-carbethoxy-6-(2,2-dimethylhydrazono)hex-2-cis-enyl]cyclopent-2-en-1-one | dl-16-hydroxy-1-carbethoxy-1,9-dioxo-16-cyclopropyl-2-nor-5-cis-13-trans prostadiene |
| 11 | 1-trans-tri-n-butylstannyl-4-trimethylsilylethynyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-ethynyl-20-nor-2-nor-5-cis-13-trans prostadiene |
| 12 | 1-trans-tri-n-butylstannyl-5-methylene-4-triethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-17-methylene-20-nor-2-nor-5-cis-13-trans prostadiene |
| 13 | 1-trans-tri-n-butylstannyl-4-methyl-5-methylene-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-17-methylene-20-nor-2-nor-5-cis-13-trans prostadiene |
| 14 | 1-trans-tri-n-butylstannyl-4-dimethoxymethyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-formyl-20-nor-2-nor-5-cis-13-trans prostadiene |
| 15 | 1-trans-tri-n-butylstannyl-4-fluoromethyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-fluoromethyl-20-nor-2-nor-5-cis-13-trans prostadiene |
| 16 | 1-trans-tri-n-butylstannyl-4-difluoromethyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-difluoromethyl-20-nor-2-nor-5-cis-13-trans prostadiene |
| 17 | 1-trans-tri-n-butylstannyl-4-trifluoromethyl-4-trimethylsilyloxy-1-heptene | 2-[6-carbethoxy-6-(2,2-dimethylhydrazono)hex-2-cis-enyl]cyclopent-2-en-1-one | dl-16-hydroxy-1-carbethoxy-1,9-dioxo-16-trifluoromethyl-20-nor-2-nor-5-cis-13-trans prostadiene |

-continued

| EXAMPLE | VINYL TIN / VINYL IODIDE | CYCLOPENTENONE | PRODUCT PROSTAGLANDIN OF THE 11-DEOXY PGE2 SERIES |
|---|---|---|---|
| 18 | 1-trans-tri-n-butylstannyl-4-chloromethyl-4-trimethylsilyloxy-1-heptene | 2-[6-carbethoxy-6-(2,2-dimethylhydrazono) hex-2-cis-enyl] cyclopent-2-en-1-one | dl-16-hydroxy-1-carbethoxy-1,9-dioxo-16-chloromethyl-20-nor-2-nor-5-cis-13-trans prostadiene |
| 19 | 1-trans-tri-n-butylstannyl-4-trimethylsilyloxymethyl-4-trimethylsilyloxy-1-heptene | 2-[6-carbethoxy-6-(2,2-dimethylhydrazono) hex-2-cis-enyl] cyclopent-2-en-1-one | dl-16-hydroxy-1-carbethoxy-1,9-dioxo-16-hydroxymethyl-20-nor-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 20 | 1-trans-iodo-4-triphenylmethoxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-2-nor-5-cis-13-trans prostadiene |
| EXAMPLE | VINYL TIN | CYCLOPENTENONE | PRODUCT PROSTAGLANDIN OF THE 11-DEOXY PGE2 SERIES |
| 21 | 1-trans-tri-n-butylstannyl-4-methyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-methyl-2-nor-5-cis-13-trans prostadiene |
| 22 | 1-trans-tri-n-butylstannyl-5-methyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-17-methyl-2-nor-5-cis-13-trans prostadiene |
| 23 | 1-trans-tri-n-butylstannyl-4-vinyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-vinyl-2-nor-5-cis-13-trans prostadiene |
| 24 | 1-trans-tri-n-butylstannyl-4-trimethylsilylethynyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-ethynyl-2-nor-5-cis-13-trans prostadiene |
| 25 | 1-trans-tri-n-butylstannyl-5-methylene-4-triethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-17-methylene-2-nor-5-cis-13-trans prostadiene |
| 26 | 1-trans-tri-n-butylstannyl-4-methyl-5-methylene-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-methyl-17-methylene-2-nor-5-cis-13-trans prostadiene |
| 27 | 1-trans-tri-n-butylstannyl-4-dimethoxymethyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-formyl-2-nor-5-cis-13-trans prostadiene |
| 28 | 1-trans-tri-n-butylstannyl-4-fluoromethyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-fluoromethyl-2-nor-5-cis-13-trans prostadiene |
| 29 | 1-trans-tri-n-butylstannyl-4-difluoromethyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-difluoromethyl-2-nor-5-cis-13-trans prostadiene |
| 30 | 1-trans-tri-n-butylstannyl-4-trifluoromethyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-trifluoromethyl-2-nor-5-cis-13-trans prostadiene |
| 31 | 1-trans-tri-n-butylstannyl-4-chloromethyl-4-trimethylsilyloxy-1-octene | 2-[6-carbethoxy-6-(2,2-dimethylhydrazono) hex-2-cis-enyl] cyclopent-2-en-1-one | dl-16-hydroxy-1-carbethoxy-1,9-dioxo-16-chloromethyl-2-nor-5-cis-13-trans prostadiene |
| EXAMPLE | VINYL IODIDE | CYCLOPENTENONE | PRODUCT PROSTAGLANDIN OF THE 11-DEOXY PGE2 SERIES |
| 32 | 1-trans-iodo-4-methyl-7-chloro-4-trimethylsilyloxy-1-heptene | 2-[6-carbethoxy-6-(2,2-dimethylhydrazono) hex-2-cis-enyl] cyclopent-2-en-1-one | dl-16-hydroxy-1-carbethoxy-1,9-dioxo-16-methyl-19-chloro-2-nor-20-nor-5-cis-13-trans prostadiene |

| EXAMPLE | VINYL TIN | cyclopent-2-en-1-one | dl-16-hydroxy-1-carbethoxy-1,9-dioxo-16-chloromethyl-2-nor-5-cis-13-trans prostadiene |
|---|---|---|---|
| | | | PRODUCT PROSTAGLANDIN OF THE 11-DEOXY PGE2 SERIES |
| 33 | 1-trans-tri-n-butylstannyl-4-trimethylsilyloxymethyl-4-trimethylsilyloxy-1-octene | 2-[6-carbethoxy-6-(2,2-dimethylhydrazono)hex-2-cis-enyl] cyclopent-2-en-1-one | dl-16-hydroxy-1-carbethoxy-1,9-dioxo-16-hydroxymethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 34 | 1-trans-iodo-4-triphenylmethoxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-20-methyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 35 | 1-trans-tri-n-butylstannyl-4-methyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-methyl-20-methyl-2-nor-5-cis-13-trans prostadiene |
| 36 | 1-trans-tri-n-butylstannyl-5-methyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-17-methyl-20-methyl-2-nor-5-cis-13-trans prostadiene |
| 37 | 1-trans-tri-n-butylstannyl-4-vinyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-vinyl-20-methyl-2-nor-5-cis-13-trans prostadiene |
| 38 | 1-trans-tri-n-butylstannyl-4-trimethylsilylethynyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-ethynyl-20-methyl-2-nor-5-cis-13-trans prostadiene |
| 39 | 1-trans-tri-n-butylstannyl-5-methylene-4-triethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-17-methylene-20-methyl-2-nor-5-cis-13-trans prostadiene |
| 40 | 1-trans-tri-n-butylstannyl-4-methyl-5-methylene-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-methyl-17-methylene-20-methyl-2-nor-5-cis-13-trans prostadiene |
| 41 | 1-trans-tri-n-butylstannyl-4-dimethoxymethyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-formyl-20-methyl-2-nor-5-cis-13-trans prostadiene |
| 42 | 1-trans-tri-n-butylstannyl-4-fluoromethyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-fluoromethyl-20-methyl-2-nor-5-cis-13-trans prostadiene |
| 43 | 1-trans-tri-n-butylstannyl-4-difluoromethyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-difluoromethyl-20-methyl-2-nor-5-cis-13-trans prostadiene |
| 44 | 1-trans-tri-n-butylstannyl-4-trifluoromethyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-trifluoromethyl-20-methyl-2-nor-5-cis-13-trans prostadiene |
| 45 | 1-trans-tri-n-butylstannyl-4-chloromethyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-chloromethyl-20-methyl-2-nor-5-cis-13-trans prostadiene |
| 46 | 1-trans-tri-n-butylstannyl-4-trimethylsilyloxymethyl-4-trimethylsilyloxy-1-nonene | 2-[6-carbethoxy-6-(2,2-dimethylhydrazono)hex-2-cis-enyl] cyclopent-2-en-1-one | dl-16-hydroxy-1-carbethoxy-1,9-dioxo-16-hydroxymethyl-20-methyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 47 | 1-trans-iodo-4-triphenylmethoxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-20-ethyl-2-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 48 | 1-trans-tri-n-butylstannyl-4-methyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-20-ethyl-2-nor-5-cis-13-trans prostadiene |
| 49 | 1-trans-tri-n-butylstannyl-5-methyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-17-methyl-20-ethyl-2-nor-5-cis-13-trans prostadiene |
| 50 | 1-trans-tri-n-butylstannyl-4-vinyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-vinyl-20-ethyl-2-nor-5-cis-13-trans prostadiene |
| 51 | 1-trans-tri-n-butylstannyl-4-trimethylsilylethynyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-ethynyl-20-ethyl-2-nor-5-cis-13-trans prostadiene |
| 52 | 1-trans-tri-n-butylstannyl-5-methylene-4-triethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-17-methylene-20-ethyl-2-nor-5-cis-13-trans prostadiene |
| 53 | 1-trans-tri-n-butylstannyl-4-methyl-5-methylene-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-17-methylene-20-ethyl-2-nor-5-cis-13-trans prostadiene |
| 54 | 1-trans-tri-n-butylstannyl-4-dimethoxymethyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-formyl-20-ethyl-2-nor-5-cis-13-trans prostadiene |
| 55 | 1-trans-tri-n-butylstannyl-4-fluoromethyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-fluoromethyl-20-ethyl-2-nor-5-cis-13-trans prostadiene |
| 56 | 1-trans-tri-n-butylstannyl-4-difluoromethyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-difluoromethyl-20-ethyl-2-nor-5-cis-13-trans prostadiene |
| 57 | 1-trans-tri-n-butylstannyl-4-trifluoromethyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-trifluoromethyl-20-ethyl-2-nor-5-cis-13-trans prostadiene |
| 58 | 1-trans-tri-n-butylstannyl-4-chloromethyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-chloromethyl-20-ethyl-2-nor-5-cis-13-trans prostadiene |
| 59 | 1-trans-tri-n-butylstannyl-4-trimethylsilyloxymethyl-4-trimethylsilyloxy-1-decene | 2-[6-carbethoxy-6-(2,2-dimethylhydrazono)hex-2-cis-enyl]cyclopent-2-en-1-one | dl-16-hydroxy-1-carbethoxy-1,9-dioxo-16-hydroxymethyl-20-ethyl-2-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 60 | 1-trans-iodo-4-triphenylmethoxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-20-nor-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|

| EXAMPLE | VINYL IODIDE | -continued | PRODUCT PROSTAGLANDIN OF THE 11-DEOXY PGE2 SERIES |
|---|---|---|---|
| 61 | 1-trans-tri-n-butylstannyl-4-ethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-ethyl-5-cis-13-trans prostadiene |
| 62 | 1-trans-tri-n-butylstannyl-5-methyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-17-methyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 63 | 1-trans-iodo-5,5-dimethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-17,17-dimethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 64 | 1-trans-tri-n-butylstannyl-4-vinyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-vinyl-20-nor-5-cis-13-trans prostadiene |
| 65 | 1-trans-tri-n-butylstannyl-4-cyclopropyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-cyclopropyl-5-cis-13-trans prostadiene |
| 66 | 1-trans-tri-n-butylstannyl-4-trimethylsilylethynyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-ethynyl-20-nor-5-cis-13-trans prostadiene |
| 67 | 1-trans-tri-n-butylstannyl-5-methylene-4-triethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-17-methylene-20-nor-5-cis-13-trans prostadiene |
| 68 | 1-trans-tri-n-butylstannyl-4-methyl-5-methylene-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-17-methylene-20-nor-5-cis-13-trans prostadiene |
| 69 | 1-trans-tri-n-butylstannyl-4-dimethoxymethyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-formyl-20-nor-5-cis-13-trans prostadiene |
| 70 | 1-trans-tri-n-butylstannyl-4-fluoromethyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-fluoromethyl-20-nor-5-cis-13-trans prostadiene |
| 71 | 1-trans-tri-n-butylstannyl-4-difluoromethyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-difluoromethyl-20-nor-5-cis-13-trans prostadiene |
| 72 | 1-trans-tri-n-butylstannyl-4-trifluoromethyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-trifluoromethyl-20-nor-5-cis-13-trans prostadiene |
| 73 | 1-trans-tri-n-butylstannyl-4-chloromethyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-chloromethyl-20-nor-5-cis-13-trans prostadiene |
| 74 | 1-trans-tri-n-butylstannyl-4-trimethylsilyloxymethyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-hydroxymethyl-20-nor-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 75 | 1-trans-iodo-4-methyl-7-chloro-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-19-chloro-20-nor-5-cis-13-trans prostadiene |

-continued

| EXAMPLE | VINYL TIN | CYCLOPENTENONE | PRODUCT PROSTAGLANDIN OF THE 11-DEOXY PGE2 SERIES |
|---|---|---|---|
| | | cyclopent-2-en-1-one | |
| 76 | 1-trans-tri-n-butylstannyl-4-methyl-4-trimethylsilyloxy-1-heptene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-20-nor-5-cis-13-trans prostadiene |
| 77 | 1-trans-tri-n-butylstannyl-5-methyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-17-methyl-5-cis-13-trans prostadiene |
| 78 | 1-trans-tri-n-butylstannyl-4-vinyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-vinyl-5-cis-13-trans prostadiene |
| 79 | 1-trans-tri-n-butylstannyl-4-trimethylsilylethynyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-ethynyl-5-cis-13-trans prostadiene |
| 80 | 1-trans-tri-n-butylstannyl-5-methylene-4-triethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-17-methylene-5-cis-13-trans prostadiene |
| 81 | 1-trans-tri-n-butylstannyl-4-methyl-5-methylene-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-17-methylene-5-cis-13-trans prostadiene |
| 82 | 1-trans-tri-n-butylstannyl-4-dimethoxymethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-formyl-5-cis-13-trans prostadiene |
| 83 | 1-trans-tri-n-butylstannyl-4-fluoromethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-fluoromethyl-5-cis-13-trans prostadiene |
| 84 | 1-trans-tri-n-butylstannyl-4-difluoromethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-difluoromethyl-5-cis-13-trans prostadiene |
| 85 | 1-trans-tri-n-butylstannyl-4-trifluoromethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-trifluoromethyl-5-cis-13-trans prostadiene |
| 86 | 1-trans-tri-n-butylstannyl-4-chloromethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-chloromethyl-5-cis-13-trans prostadiene |
| 87 | 1-trans-tri-n-butylstannyl-4-trimethylsilyloxymethyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-hydroxymethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 88 | 1-trans-iodo-4-triphenylmethoxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-5-cis-13-trans prostadiene |

| EXAMPLE | VINYL TIN | THE 11-DEOXY PGE2 SERIES | PRODUCT PROSTAGLANDIN OF |
|---|---|---|---|
| 89 | 1-trans-tri-n-butylstannyl-4-methyl-4-trimethylsilyloxy-1-octene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-5-cis-13-trans prostadiene |

-continued

| EXAMPLE | VINYL IODIDE | CYCLOPENTENONE | PRODUCT PROSTAGLANDIN OF THE 11-DEOXY PGE2 SERIES |
|---|---|---|---|
| 90 | 1-trans-iodo-4-triphenylmethoxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-20-methyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 91 | 1-trans-tri-n-butylstannyl-4-vinyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-vinyl-20-methyl-5-cis-13-trans prostadiene |
| 92 | 1-trans-tri-n-butylstannyl-4-trimethylsilylethynyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-ethynyl-20-methyl-5-cis-13-trans prostadiene |
| 93 | 1-trans-tri-n-butylstannyl-5-methylene-4-triethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-17-methylene-20-methyl-5-cis-13-trans prostadiene |
| 94 | 1-trans-tri-n-butylstannyl-4-methyl-5-methylene-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-methyl-17-methylene-20-methyl-5-cis-13-trans prostadiene |
| 95 | 1-trans-tri-n-butylstannyl-4-dimethoxymethyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-formyl-20-methyl-5-cis-13-trans prostadiene |
| 96 | 1-trans-tri-n-butylstannyl-4-fluoromethyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-fluoromethyl-20-methyl-5-cis-13-trans prostadiene |
| 97 | 1-trans-tri-n-butylstannyl-4-difluoromethyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-difluoromethyl-20-methyl-5-cis-13-trans prostadiene |
| 98 | 1-trans-tri-n-butylstannyl-4-trifluromethyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-trifluoromethyl-20-methyl-5-cis-13-trans prostadiene |
| 99 | 1-trans-tri-n-butylstannyl-4-chloromethyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-chloromethyl-20-methyl-5-cis-13-trans prostadiene |
| 100 | 1-trans-tri-n-butylstannyl-4-trimethylsilyloxymethyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-hydroxymethyl-20-methyl-5-cis-13-trans prostadiene |
| 101 | 1-trans-tri-n-butylstannyl-4-methyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-16-methyl-20-methyl-5-cis-13-trans prostadiene |
| 102 | 1-trans-tri-n-butylstannyl-5-methyl-4-trimethylsilyloxy-1-nonene | 2-[7-carbethoxy-7-(2,2-dimethylhydrazono)hept-2-cis-enyl] cyclopent-2-en-1-one | dl-16-hydroxy-1-carbethoxy-1,9-dioxo-17-methyl-20-methyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 103 | 1-trans-iodo-4-triphenylmethoxy-1-decene | 2-[7-carbethoxy-7-(2,2-dimethylhydrazono)hept-2-cis-enyl] cyclopent-2-en-1-one | dl-16-hydroxy-1-carbethoxy-1,9-dioxo-20-ethyl-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|

| | | | |
|---|---|---|---|
| 104 | 1-trans-tri-n-butylstannyl-4-methyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-20-ethyl-5-cis-13-trans prostadiene |
| 105 | 1-trans-tri-n-butylstannyl-5-methyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-17-methyl-20-ethyl-5-cis-13-trans prostadiene |
| 106 | 1-trans-tri-n-butylstannyl-4-vinyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-vinyl-20-ethyl-5-cis-13-trans prostadiene |
| 107 | 1-trans-tri-n-butylstannyl-4-trimethylsilylethynyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-ethynyl-20-ethyl-5-cis-13-trans prostadiene |
| 108 | 1-trans-tri-n-butylstannyl-5-methylene-4-triethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-17-methylene-20-ethyl-5-cis-13-trans prostadiene |
| 109 | 1-trans-tri-n-butylstannyl-4-methyl-5-methylene-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-17-methylene-20-ethyl-5-cis-13-trans prostadiene |
| 110 | 1-trans-tri-n-butylstannyl-4-dimethoxymethyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-formyl-20-ethyl-5-cis-13-trans prostadiene |
| 111 | 1-trans-tri-n-butylstannyl-4-fluoromethyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-fluoromethyl-20-ethyl-5-cis-13-trans prostadiene |
| 112 | 1-trans-tri-n-butylstannyl-4-difluoromethyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-difluoromethyl-20-ethyl-5-cis-13-trans prostadiene |
| 113 | 1-trans-tri-n-butylstannyl-4-trifluoromethyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-trifluoromethyl-20-ethyl-5-cis-13-trans prostadiene |
| 114 | 1-trans-tri-n-butylstannyl-4-chloromethyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-chloromethyl-20-ethyl-5-cis-13-trans prostadiene |
| 115 | 1-trans-tri-n-butylstannyl-4-trimethylsilyloxymethyl-4-trimethylsilyloxy-1-decene | 2-[7-carbethoxy-7-(2,2-dimethylhydrazono)hept-2-cis-enyl]cyclopent-2-en-1-one | dl-16-hydroxy-1-carbethoxy-1,9-dioxo-16-hydroxymethyl-20-ethyl-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 116 | 1-trans-iodo-4-triphenylmethoxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-20-nor-2-homo-5-cis-13-trans prostadiene |
| 117 | 1-trans-iodo-4-triphenylmethoxy-1-octene | 2-[8-carbethoxy-8-(2,2-dimethylhydrazono)oct-2-cis-enyl]cyclopent-2-en-1-one | dl-16-hydroxy-1-carbethoxy-1,9-dioxo-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 118 | 1-trans-tri-n-butylstannyl-4-methyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-methyl-20-nor-2-homo-5-cis-13-trans prostadiene |
| 119 | 1-trans-tri-n-butylstannyl-4-ethyl-4-trimethylsilyloxy-1-octene | 2-[8-carbethoxy-8-(2,2-dimethylhydrazono)oct-2-cis-enyl]cyclopent-2-en-1-one | dl-16-hydroxy-1-carbethoxy-1,9-dioxo-16-ethyl-2-homo-5-cis-13-trans prostadiene |

| | | -continued | |
|---|---|---|---|
| 120 | 1-trans-tri-n-butylstannyl-5-methyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-17-methyl-20-nor-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 121 | 1-trans-iodo-5,5-dimethyl-4-trimethylsilyloxy-1-octene | 2-[8-carbethoxy-8-(2,2-dimethylhydrazono)oct-2-cis-enyl]cyclopent-2-en-1-one | dl-16-hydroxy-1-carbethoxy-1,9-dioxo-17,17-dimethyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 122 | 1-trans-tri-n-butylstannyl-4-vinyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-vinyl-20-nor-2-homo-5-cis-13-trans prostadiene |
| 123 | 1-trans-tri-n-butylstannyl-4-cyclopropyl-4-trimethylsilyloxy-1-octene | 2-[8-carbethoxy-8-(2,2-dimethylhydrazono)oct-2-cis-enyl]cyclopent-2-en-1-one | dl-16-hydroxy-1-carbethoxy-1,9-dioxo-16-cyclopropyl-2-homo-5-cis-13-trans prostadiene |
| 124 | 1-trans-tri-n-butylstannyl-4-trimethylsilylethynyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-ethynyl-20-nor-2-homo-5-cis-13-trans prostadiene |
| 125 | 1-trans-tri-n-butylstannyl-5-methylene-4-triethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-17-methylene-20-nor-2-homo-5-cis-13-trans prostadiene |
| 126 | 1-trans-tri-n-butylstannyl-4-methyl-5-methylene-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-methyl-17-methylene-20-nor-2-homo-5-cis-13-trans prostadiene |
| 127 | 1-trans-tri-n-butylstannyl-4-dimethoxymethyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-formyl-20-nor-2-homo-5-cis-13-trans prostadiene |
| 128 | 1-trans-tri-n-butylstannyl-4-fluoromethyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-fluoromethyl-20-nor-2-homo-5-cis-13-trans prostadiene |
| 129 | 1-trans-tri-n-butylstannyl-4-difluoromethyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-difluoromethyl-20-nor-2-homo-5-cis-13-trans prostadiene |
| 130 | 1-trans-tri-n-butylstannyl-4-trifluoromethyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-trifluoromethyl-20-nor-2-homo-5-cis-13-trans prostadiene |
| 131 | 1-trans-tri-n-butylstannyl-4-chloromethyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-chloromethyl-20-nor-2-homo-5-cis-13-trans prostadiene |
| 132 | 1-trans-tri-n-butylstannyl-4-trimethylsilyloxymethyl-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-hydroxymethyl-20-nor-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 133 | 1-trans-iodo-4-methyl-7-chloro-4-trimethylsilyloxy-1-heptene | 2-[8-carbethoxy-8-(2,2-dimethylhydrazono)oct-2-cis-enyl]cyclopent-2-en-1-one | dl-16-hydroxy-1-carbethoxy-1,9-dioxo-16-methyl-19-chloro-2-homo-20-nor-5-cis-13-trans prostadiene |
| | | | PRODUCT PROSTAGLANDIN OF |

-continued

| EXAMPLE | VINYL TIN | CYCLOPENTENONE | THE 11-DEOXY PGE2 SERIES |
|---|---|---|---|
| 134 | 1-trans-tri-n-butylstannyl-4-methyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-methyl-2-homo-5-cis-13-trans prostadiene |
| 135 | 1-trans-tri-n-butylstannyl-5-methyl-4-triethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-17-methyl-2-homo-5-cis-13-trans prostadiene |
| 136 | 1-trans-tri-n-butylstannyl-4-vinyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-vinyl-2-homo-5-cis-13-trans prostadiene |
| 137 | 1-trans-tri-n-butylstannyl-4-trimethylsilylethynyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-ethynyl-2-homo-5-cis-13-trans prostadiene |
| 138 | 1-trans-tri-n-butylstannyl-5-methylene-4-triethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-17-methylene-2-homo-5-cis-13-trans prostadiene |
| 139 | 1-trans-tri-n-butylstannyl-4-methyl-5-methylene-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-methyl-17-methylene-2-homo-5-cis-13-trans prostadiene |
| 140 | 1-trans-tri-n-butylstannyl-4-dimethoxymethyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-formyl-2-homo-5-cis-13-trans prostadiene |
| 141 | 1-trans-tri-n-butylstannyl-4-fluoromethyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-fluoromethyl-2-homo-5-cis-13-trans prostadiene |
| 142 | 1-trans-tri-n-butylstannyl-4-difluoromethyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-difluoromethyl-2-homo-5-cis-13-trans prostadiene |
| 143 | 1-trans-tri-n-butylstannyl-4-trifluoromethyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-trifluoromethyl-2-homo-5-cis-13-trans prostadiene |
| 144 | 1-trans-tri-n-butylstannyl-4-chloromethyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-chloromethyl-2-homo-5-cis-13-trans prostadiene |
| 145 | 1-trans-tri-n-butylstannyl-4-trimethylsilyloxymethyl-4-trimethylsilyloxy-1-octene | 2-[8-carbethoxy-8-(2,2-dimethylhydrazono)oct-2-cis-enyl] cyclopent-2-en-1-one | dl-16-hydroxy-1-carbethoxy-1,9-dioxo-16-hydroxymethyl-2-homo-5-cis-13-trans prostadiene |
| 146 | 1-trans-tri-n-butylstannyl-4-trimethylsilyloxymethyl-4-trimethylsilyloxy-1-nonene | 2-[8-carbethoxy-8-(2,2-dimethylhydrazono)oct-2-cis-enyl] cyclopent-2-en-1-one | dl-16-hydroxy-1-carbethoxy-1,9-dioxo-16-hydroxymethyl-20-methyl-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 147 | 1-trans-iodo-4-triphenylmethoxy-1-nonene | 2-[8-carbethoxy-8-(2,2-dimethylhydrazono)oct-2-cis-enyl] cyclopent-2-en-1-one | dl-16-hydroxy-1-carbethoxy-1,9-dioxo-20-methyl-2-homo-5-cis-13-trans prostadiene |

| EXAMPLE | VINYL TIN | CYCLOPENTENONE | PRODUCT PROSTAGLANDIN OF THE 11-DEOXY PGE2 SERIES |
|---|---|---|---|
| 148 | 1-trans-tri-n-butylstannyl-4-methyl-4-trimethylsilyloxy-1-nonene | 2-[8-carbethoxy-8-(2,2-dimethylhydrazono)oct-2-cis-enyl] cyclopent-2-en-1-one | dl-16-hydroxy-1-carbethoxy-1,9-dioxo-16-methyl-20-methyl-2-homo-5-cis-13-trans prostadiene |
| 149 | 1-trans-tri-n-butylstannyl-5-methyl | | dl-16-hydroxy-1-carbethoxy-1,9-dioxo- |

| EXAMPLE | VINYL IODIDE | CYCLOPENTENONE | PRODUCT PROSTAGLANDIN OF THE 11-DEOXY PGE2 SERIES |
|---|---|---|---|
| | 4-trimethylsilyloxy-1-nonene | oct-2-cis-enyl] cyclopent-2-en-1-one | 17-methyl-20-methyl-2-homo-5-cis-13-trans prostadiene |
| 150 | 1-trans-tri-n-butylstannyl-4-vinyl-4-trimethylsilyloxy-1-nonene | 2-[8-carbethoxy-8-(2,2-dimethylhydrazono) oct-2-cis-enyl] cyclopent-2-en-1-one | dl-16-hydroxy-1-carbethoxy-1,9-dioxo-16-vinyl-20-methyl-2-homo-5-cis-13-trans prostadiene |
| 151 | 1-trans-tri-n-butylstannyl-4-trimethylsilylethynyl-4-trimethylsilyloxy-1-nonene | 2-[8-carbethoxy-8-(2,2-dimethylhydrazono) oct-2-cis-enyl] cyclopent-2-en-1-one | dl-16-hydroxy-1-carbethoxy-1,9-dioxo-16-ethynyl-20-methyl-2-homo-5-cis-13-trans prostadiene |
| 152 | 1-trans-tri-n-butylstannyl-5-methylene-4-triethylsilyloxy-1-nonene | 2-[8-carbethoxy-8-(2,2-dimethylhydrazono) oct-2-cis-enyl] cyclopent-2-en-1-one | dl-16-hydroxy-1-carbethoxy-1,9-dioxo-16-methyl-17-methylene-20-methyl-2-homo-5-cis-13-trans prostadiene |
| 153 | 1-trans-tri-n-butylstannyl-4-methyl-5-methylene-4-trimethylsilyloxy-1-nonene | 2-[8-carbethoxy-8-(2,2-dimethylhydrazono) oct-2-cis-enyl] cyclopent-2-en-1-one | dl-16-hydroxy-1-carbethoxy-1,9-dioxo-16-formyl-20-methyl-2-homo-5-cis-13-trans prostadiene |
| 154 | 1-trans-tri-n-butylstannyl-4-dimethoxymethyl-4-trimethylsilyloxy-1-nonene | 2-[8-carbethoxy-8-(2,2-dimethylhydrazono) oct-2-cis-enyl] cyclopent-2-en-1-one | dl-16-hydroxy-1-carbethoxy-1,9-dioxo-16-fluoromethyl-20-methyl-2-homo-5-cis-13-trans prostadiene |
| 155 | 1-trans-tri-n-butylstannyl-4-fluoromethyl-4-trimethylsilyloxy-1-nonene | 2-[8-carbethoxy-8-(2,2-dimethylhydrazono) oct-2-cis-enyl] cyclopent-2-en-1-one | dl-16-hydroxy-1-carbethoxy-1,9-dioxo-16-difluoromethyl-20-methyl-2-homo-5-cis-13-trans prostadiene |
| 156 | 1-trimethylsilyl-4-difluoromethyl-4-trimethylsilyloxy-1-nonene | 2-[8-carbethoxy-8-(2,2-dimethylhydrazono) oct-2-cis-enyl] cyclopent-2-en-1-one | PRODUCT PROSTAGLANDIN OF THE 11-DEOXY PGE2 SERIES |
| EXAMPLE | VINYL IODIDE | CYCLOPENTENONE | |
| 157 | 1-trans-iodo-4-triphenylmethoxy-1-decene | 2-[8-carbethoxy-8-(2,2-dimethylhydrazono) cyclopent-2-en-1-one | dl-16-hydroxy-1-carbethoxy-1,9-dioxo-20-ethyl-2-homo-5-cis-13-trans prostadiene |
| EXAMPLE | VINYL TIN | CYCLOPENTENONE | PRODUCT PROSTAGLANDIN OF THE 11-DEOXY PGE2 SERIES |
| 158 | 1-trans-tri-n-butylstannyl-4-methyl-4-trimethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-20-ethyl-2-homo-5-cis-13-trans prostadiene |
| 159 | 1-trans-tri-n-butylstannyl-5-methyl-4-trimethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-16-vinyl-17-methyl-20-ethyl-2-homo-5-cis-13-trans prostadiene |
| 160 | 1-trans-tri-n-butylstannyl-4-vinyl-4-trimethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-16-vinyl-20-ethyl-2-homo-5-cis-13-trans prostadiene |
| 161 | 1-trans-tri-n-butylstannyl-4-trimethylsilylethynyl-4-trimethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-16-ethynyl-20-ethyl-2-homo-5-cis-13-trans prostadiene |
| 162 | 1-trans-tri-n-butylstannyl-5-methylene-4-triethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-17-methylene-20-ethyl-2-homo-5-cis-13-trans prostadiene |
| 163 | 1-trans-tri-n-butylstannyl-4-methyl-5-methylene-4-trimethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-16-methyl-17-methylene-20-ethyl-2-homo-5-cis-13-trans prostadiene |
| 164 | 1-trans-tri-n-butylstannyl-4-dimethoxymethyl-4-trimethylsilyloxy-1-decene | 2-[8-carbethoxy-8-(2,2-dimethylhydrazono) oct-2-cis-enyl] cyclopent-2-en-1-one | dl-16-hydroxy-1-carbethoxy-1,9-dioxo-16-formyl-20-ethyl-2-homo-5-cis-13-trans prostadiene |

| EXAMPLE | | -continued | |
|---|---|---|---|
| 165 | 1-trans-tri-n-butylstannyl-4-fluoromethyl-4-trimethylsilyloxy-1-decene | 2-[8-carbethoxy-8-(2,2-dimethylhydrazono)oct-2-cis-enyl]cyclopent-2-en-1-one | dl-16-hydroxy-1-carbethoxy-1,9-dioxo-16-fluoromethyl-20-ethyl-2-homo-5-cis-13-trans prostadiene |
| 166 | 1-trans-tri-n-butylstannyl-4-difluoromethyl-4-trimethylsilyloxy-1-decene | 2-[8-carbethoxy-8-(2,2-dimethylhydrazono)oct-2-cis-enyl]cyclopent-2-en-1-one | dl-16-hydroxy-1-carbethoxy-1,9-dioxo-16-difluoromethyl-20-ethyl-2-homo-5-cis-13-trans prostadiene |
| 167 | 1-trans-tri-n-butylstannyl-4-trifluoromethyl-4-trimethylsilyloxy-1-decene | 2-[8-carbethoxy-8-(2,2-dimethylhydrazono)oct-2-cis-enyl]cyclopent-2-en-1-one | dl-16-hydroxy-1-carbethoxy-1,9-dioxo-16-trifluoromethyl-20-ethyl-2-homo-5-cis-13-trans prostadiene |
| 168 | 1-trans-tri-n-butylstannyl-4-chloromethyl-4-trimethylsilyloxy-1-decene | 2-[8-carbethoxy-8-(2,2-dimethylhydrazono)oct-2-cis-enyl]cyclopent-2-en-1-one | dl-16-hydroxy-1-carbethoxy-1,9-dioxo-16-chloromethyl-20-ethyl-2-homo-5-cis-13-trans prostadiene |
| 169 | 1-trans-tri-n-butylstannyl-4-trimethylsilyloxymethyl-4-trimethylsilyloxy-1-decene | 2-[8-carbethoxy-8-(2,2-dimethylhydrazono)oct-2-cis-enyl]cyclopent-2-en-1-one | dl-16-hydroxy-1-carbethoxy-1,9-dioxo-16-hydroxymethyl-20-ethyl-2-homo-5-cis-13-trans prostadiene |
| 170 | 1-trans-tri-n-butylstannyl-4-trifluoromethyl-4-trimethylsilyloxy-1-nonene | 2-[8-carbethoxy-8-(2,2-dimethylhydrazono)oct-2-cis-enyl]cyclopent-2-en-1-one | dl-16-hydroxy-1-carbethoxy-1,9-dioxo-16-trifluoromethyl-20-methyl-2-homo-5-cis-13-trans prostadiene |

| EXAMPLE | VINYL IODIDE | CYCLOPENTENONE | PRODUCT PROSTAGLANDIN OF THE 11-DEOXY PGE2 SERIES |
|---|---|---|---|
| 171 | 1-trans-iodo-4-triphenylmethoxy-1,5-heptadiene | 2-[6-carbethoxy-6-(2,2-dimethylhydrazono)hex-2-cis-enyl]cyclopent-2-en-1-one | dl-16-hydroxy-1-carbethoxy-1,9-dioxo-20-nor-2-nor-5-cis-13-trans-17-trans prostatriene |
| 172 | 1-trans-iodo-4-methyl-4-trimethylsilyloxy-1,5-heptadiene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-20-nor-2-nor-5-cis-13-trans-17-trans prostatriene |
| 173 | 1-trans-iodo-4-triphenylmethoxy-1,5-octadiene | 2-[6-carbethoxy-6-(2,2-dimethylhydrazono)hex-2-cis-enyl]cyclopent-2-en-1-one | dl-16-hydroxy-1-carbethoxy-1,9-dioxo-2-nor-5-cis-13-trans-17-trans prostatriene |
| 174 | 1-trans-iodo-4-methyl-4-trimethylsilyloxy-1,5-octadiene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-2-nor-5-cis-13-trans-17-trans prostatriene |
| 175 | 1-trans-iodo-4-triphenylmethoxy-1,5-nonadiene | 2-[6-carbethoxy-6-(2,2-dimethylhydrazono)hex-2-cis-enyl]cyclopent-2-en-1-one | dl-16-hydroxy-1-carbethoxy-1,9-dioxo-20-methyl-2-nor-5-cis-13-trans-17-trans prostatriene |
| 176 | 1-trans-iodo-4-methyl-4-trimethylsilyloxy-1,5-nonadiene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-20-methyl-2-nor-5-cis-13-trans-17-trans prostatriene |
| 177 | 1-trans-iodo-4-triphenylmethoxy-1,5-decadiene | 2-[6-carbethoxy-6-(2,2-dimethylhydrazono)hex-2-cis-enyl]cyclopent-2-en-1-one | dl-16-hydroxy-1-carbethoxy-1,9-dioxo-20-ethyl-2-nor-5-cis-13-trans-17-trans prostatriene |
| 178 | 1-trans-iodo-4-methyl-4-trimethylsilyloxy-1,5-decadiene | 2-[6-carbethoxy-6-(2,2-dimethylhydrazono)hex-2-cis-enyl]cyclopent-2-en-1-one | dl-16-hydroxy-1-carbethoxy-1,9-dioxo-16-methyl-20-ethyl-2-nor-5-cis-13-trans-17-trans prostatriene |
| 179 | 1-trans-iodo-4-triphenylmethoxy-1,5-heptadiene | 2-[7-carbethoxy-7-(2,2-dimethylhydrazono)hept-2-cis-enyl]cyclopent-2-en-1-one | dl-16-hydroxy-1-carbethoxy-1,9-dioxo-20-nor-5-cis-13-trans-17-trans prostatriene |
| 180 | 1-trans-iodo-4-methyl-4-trimethylsilyloxy-1,5-heptadiene | 2-[7-carbethoxy-7-(2,2-dimethylhydrazono)hept-2-cis-enyl]cyclopent-2-en-1-one | dl-16-hydroxy-1-carbethoxy-1,9-dioxo-16-methyl-20-nor-5-cis-13-trans-17-trans prostatriene |
| 181 | 1-trans-iodo-4-triphenylmethoxy-1,5-octadiene | 2-[7-carbethoxy-7-(2,2-dimethylhydrazono)hept-2-cis-enyl]cyclopent-2-en-1-one | dl-16-hydroxy-1-carbethoxy-1,9-dioxo-5-cis-13-trans-17-trans prostatriene |

| EXAMPLE | VINYL TIN | CYCLOPENTENONE | PRODUCT PROSTAGLANDIN OF THE 11-DEOXY PGE2 SERIES |
|---|---|---|---|
| 182 | 1-trans-iodo-4-methyl-4-trimethylsilyloxy-1,5-octadiene | 2-[7-carbethoxy-7-(2,2-dimethylhydrazono)cyclopent-2-en-1-one hept-2-cis-enyl] | dl-16-hydroxy-1-carbethoxy-1,9-dioxo-16-methyl-5-cis-13-trans-17-trans prostatriene |
| 183 | 1-trans-iodo-4-triphenylmethoxy-1,5-nonadiene | 2-[7-carbethoxy-7-(2,2-dimethylhydrazono)cyclopent-2-en-1-one hept-2-cis-enyl] | dl-16-hydroxy-1-carbethoxy-1,9-dioxo-20-methyl-5-cis-13-trans-17-trans prostatriene |
| 184 | 1-trans-iodo-4-methyl-4-trimethylsilyloxy-1,5-nonadiene | 2-[7-carbethoxy-7-(2,2-dimethylhydrazono)cyclopent-2-en-1-one hept-2-cis-enyl] | dl-16-hydroxy-1-carbethoxy-1,9-dioxo-16-methyl-20-methyl-5-cis-13-trans-17-trans prostatriene |
| 185 | 1-trans-iodo-4-triphenylmethoxy-1,5-decadiene | 2-[7-carbethoxy-7-(2,2-dimethylhydrazono)cyclopent-2-en-1-one hept-2-cis-enyl] | dl-16-hydroxy-1-carbethoxy-1,9-dioxo-20-ethyl-5-cis-13-trans-17-trans prostatriene |
| 186 | 1-trans-iodo-4-methyl-4-trimethylsilyloxy-1,5-decadiene | 2-[7-carbethoxy-7-(2,2-dimethylhydrazono)cyclopent-2-en-1-one hept-2-cis-enyl] | dl-16-hydroxy-1-carbethoxy-1,9-dioxo-16-methyl-20-ethyl-5-cis-13-trans-17-trans prostatriene |
| 187 | 1-trans-iodo-4-triphenylmethoxy-1,5-heptadiene | 2-[8-carbethoxy-8-(2,2-dimethylhydrazono)cyclopent-2-en-1-one oct-2-cis-enyl] | dl-16-hydroxy-1-carbethoxy-1,9-dioxo-20-nor-2-homo-5-cis-13-trans-17-trans prostatriene |
| 188 | 1-trans-iodo-4-methyl-4-trimethylsilyloxy-1,5-heptadiene | 2-[8-carbethoxy-8-(2,2-dimethylhydrazono)cyclopent-2-en-1-one oct-2-cis-enyl] | dl-16-hydroxy-1-carbethoxy-1,9-dioxo-16-methyl-20-nor-2-homo-5-cis-13-trans-17-trans prostatriene |
| 189 | 1-trans-iodo-4-triphenylmethoxy-1,5-octadiene | 2-[8-carbethoxy-8-(2,2-dimethylhydrazono)cyclopent-2-en-1-one oct-2-cis-enyl] | dl-16-hydroxy-1-carbethoxy-1,9-dioxo-2-homo-5-cis-13-trans-17-trans prostatriene |
| 190 | 1-trans-iodo-4-methyl-4-trimethylsilyloxy-1,5-octadiene | 2-[8-carbethoxy-8-(2,2-dimethylhydrazono)cyclopent-2-en-1-one oct-2-cis-enyl] | dl-16-hydroxy-1-carbethoxy-1,9-dioxo-16-methyl-2-homo-5-cis-13-trans-17-trans prostatriene |
| 191 | 1-trans-iodo-4-triphenylmethoxy-1,5-nonadiene | 2-[8-carbethoxy-8-(2,2-dimethylhydrazono)cyclopent-2-en-1-one oct-2-cis-enyl] | dl-16-hydroxy-1-carbethoxy-1,9-dioxo-20-methyl-2-homo-5-cis-13-trans-17-trans prostatriene |
| 192 | 1-trans-iodo-4-methyl-4-trimethylsilyloxy-1,5-nonadiene | 2-[8-carbethoxy-8-(2,2-dimethylhydrazono)cyclopent-2-en-1-one oct-2-cis-enyl] | dl-16-hydroxy-1-carbethoxy-1,9-dioxo-16-methyl-20-methyl-2-homo-5-cis-13-trans-17-trans prostatriene |
| 193 | 1-trans-iodo-4-triphenylmethoxy-1,5-decadiene | 2-[8-carbethoxy-8-(2,2-dimethylhydrazono)cyclopent-2-en-1-one oct-2-cis-enyl] | dl-16-hydroxy-1-carbethoxy-1,9-dioxo-20-ethyl-2-homo-5-cis-13-trans-17-trans prostatriene |
| 194 | 1-trans-iodo-4-methyl-4-trimethylsilyloxy-1,5-decadiene | 2-[8-carbethoxy-8-(2,2-dimethylhydrazono)cyclopent-2-en-1-one oct-2-cis-enyl] | dl-16-hydroxy-1-carbethoxy-1,9-dioxo-16-methyl-20-ethyl-2-homo-5-cis-13-trans-17-trans prostatriene |

| EXAMPLE | VINYL TIN | CYCLOPENTENONE | PRODUCT PROSTAGLANDIN OF THE 11-DEOXY PGE2 SERIES |
|---|---|---|---|
| 195 | 1-trans-tri-n-butylstannyl-4-chloromethyl-4-trimethylsilyloxy-1-nonene | 2-[8-carbethoxy-8-(2,2-dimethylhydrazono)cyclopent-2-en-1-one oct-2-cis-enyl] | dl-16-hydroxy-1-carbethoxy-1,9-dioxo-16-chloromethyl-20-methyl-2-homo-5-cis-13-trans prostadiene |

EXAMPLE 196

Gastric Acid Secretion in the Dog

Experiments are carried out on six fasted female mongrel dogs, 3–7 years of age. Each had been provided with either a gastric fistula (4 dogs) or a Heidenhain pouch (2 dogs) using standard surgical techniques. Briefly, spool shaped cannulae of stainless steel (gastric fistula preparation) or titanium (Heidenhain pouch preparation) were inserted into narrow slits in the most dependent portion of the ventral stomach and retained in place by a purse-string suture. In the Heidenhain pouch preparation the slit made in a denervated sleeve of stomach which was isolated along the greater curvature. The cannulae were exteriorized through a trocar wound in the abdomen just left of midline and, as the purse string was tightened about the cannulae, the edges of the wound were inverted.

A. Gastric Fistula Dogs-Dosing and Sample Collection

The drug is administered at zero time through the smaller lumen of a double lumen Salem Sump Tube which has been placed transorally into the animal's stomach. The length is adjusted to reach from the mouth just to the cannula site. Five ml of saline are then flushed through the same smaller lumen, followed by 5 ml of air. Immediately following 20–25 ml of saline are placed into the stomach through the larger lumen of the double lumen tube and the tube withdrawn.

Thirty minutes after the drug is administered the gastric annula is opened, irrigated rapidly with 25–30 ml of saline 4 separate times and allowed to drain for 15 minutes.

At the end of the drainage period, the intravenous histamine infusion is started (40 g/kg/hr) and the first 15 minutes collection period of gastric secretions via the cannula is begun. The collection is changed every 15 minutes. The volume of each 15 minute sample is measured and an aliquot titrated to pH 7 with 0.1 N NaOH using a Radiometer automatic titrator.

B. Heidenhain Pouch Dogs-Dosing and Sample Collections

The intravenous histamine infusion (40 g/kg/hr) is started. At the same time, the first gastric secretion collection is begun. These secretions are collected by gravity drainage through the Heidenhain pouch cannula. Separate gastric samples are collected every fifteen minutes. When the volumes of two successive samples are within 10% of each other (usually occurring by the end of the fourth period—after one hour of histamine infusion) the drug is given to the animal (time 0). The latter of the two samples is considered to be the control for that particular experiment. The drug is administered through the smaller lumen of a double lumen Salem Sump Tube which has been cut to a length equal to the mouth to stomach distance of the dog. Following administration of the drug, the narrow lumen is flushed first with 5 ml of saline, followed by 5 ml of air. Twenty-five to 30 ml of saline is then introduced into the stomach through the larger lumen and the tube withdrawn. (Note: Samples of gastric juice are taken form the pouch, drug is administered into the main stomach). Aliquots of each 15 minute gastric sample are titrated to pH 7 with 0.1 N NaOH using a Radio-meter automatic titrator.

EXAMPLE 197

The compounds of this invention are useful as bronchodilators for the treatment of asthma and chronic bronchitis. Bronchodilator activity is determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, *Arzneimittel-Forschung*, 18, 955 (1968).]

In Table which follows bronchodilator activity for representative compounds of this invention against one or more of three spasmogenic agents is expressed as an $ED_{50}$ determined from the results obtained with three logarithmic cummulative intravenous doses. In this assay, these compounds of this invention provide an effect of longer duration than does natural 1-PGE$_1$ or 1-PGE$_2$.

| COMPOUND | $ED_{50}$(Mg/kg × 10$^{-6}$) | | |
|---|---|---|---|
| | 5HT | HIST. | ACH |
| dl-1,9-dioxo-1-carbethoxy-11α, 16-dihydroxy-16-vinyl-5-cis-13-trans prostadiene | 665 | 2260 | 3410 |
| dl-1,9-dioxo-1-carbethoxy-11α, 16-dihydroxy-16-methyl-5-cis-13-trans-prostadiene | 9510 | 9310 | 5920 |
| dl-1,9-dioxo-1-carbethoxy-11α, 15-dihydroxy-15-methyl-13-trans-prostene | 4220 | 6050 | >3.2 |

| COMPOUND | ASSAY | 9% INHIBITION ACID SECRETION Time after compound (minutes) | | | | | | | |
|---|---|---|---|---|---|---|---|---|---|
| | | 0–15 | 15–30 | 30–45 | 45–60 | 60—75 | 75–90 | 9014 105 | 105–120 |
| dl-1,9-dioxo-1-carbethoxy-11,16-dihydroxy-16-methyl-5-cis-13-trans-prostadiene | Dog Gastric[1] Fistula | — | — | — | 96 | 62 | 59 | 56 | 47 |
| dl-1,9-dioxo-1-carbethoxy-11,16-dihydroxy-16-methyl-13-trans-prostene | Dog Gastric[1] Fistula | — | — | — | 97 | 91 | 76 | 72 | 56 |
| dl-1,9-dioxo-1-carbethoxy-11,16-dihydroxy-16-methyl-13-trans-prostene | Dog Heidenhain Pouch | 20 | 28 | 34 | 21 | 12 | | | |

[1]Secretion is stimulated with intravenous histamine, 40 μg/kg/hr, starting 45 minutes after administration of compound (5μg/Kg) or vehicle (control) by stomach tube. Secretions are collected from fistula annula.

[2]Seretion is stimulated with intravenous histamine, 40 μg/kg/hr, and samples are collected through the pouch cannula at 15 minute intevals. When the volume of two successive samplesare within 10% of each other, compound is administered (5 μg/kg) by stomach tube. The end of the latter two periods is considered as 0 time (control).

FLOWSHEET A
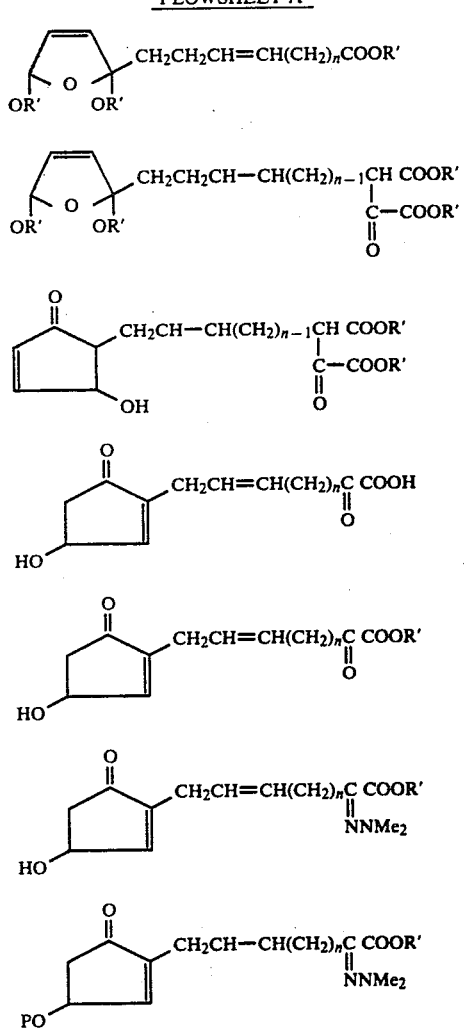
FLOWSHEET B
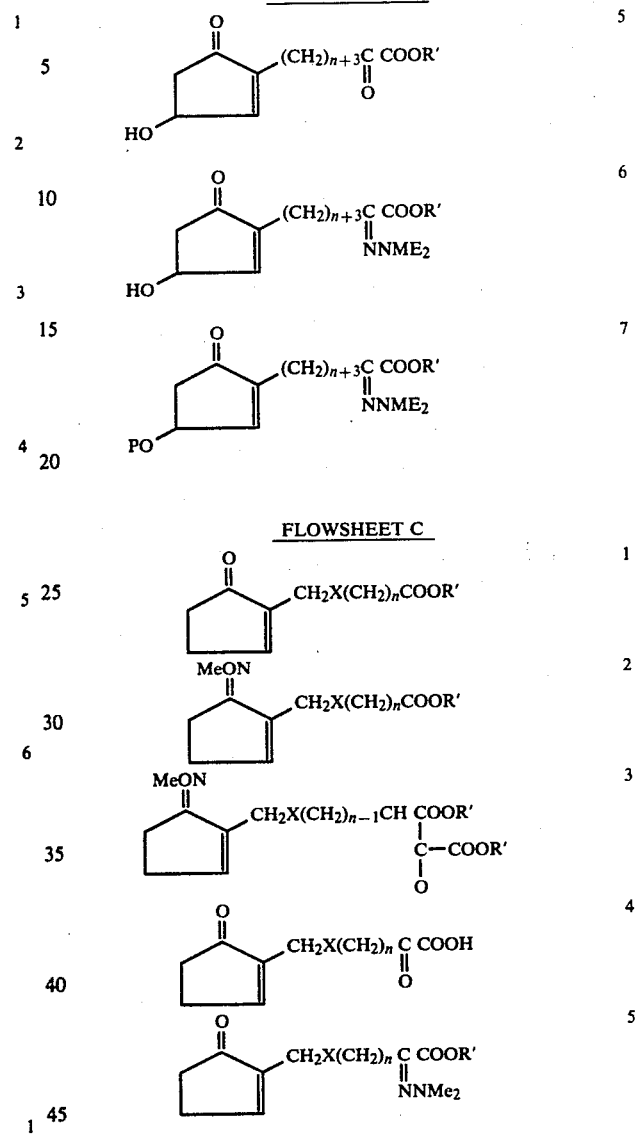
FLOWSHEET C
What is claimed:
1. A compound of the formula
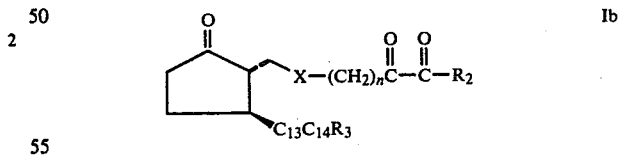
wherein $R_2$ is selected from the group hydroxy and $C_1$ to $C_7$ alkoxy; X is selected from the group cis or trans —CH=CH—; $C_{13}$-$C_{14}$ is trans —CH=CH—; n is the integer 3, 4 or 5; and $R_3$ is selected from the group
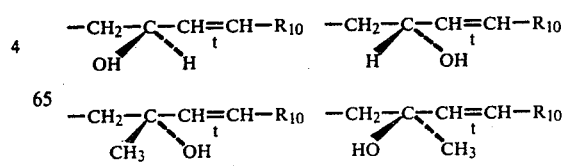

-continued

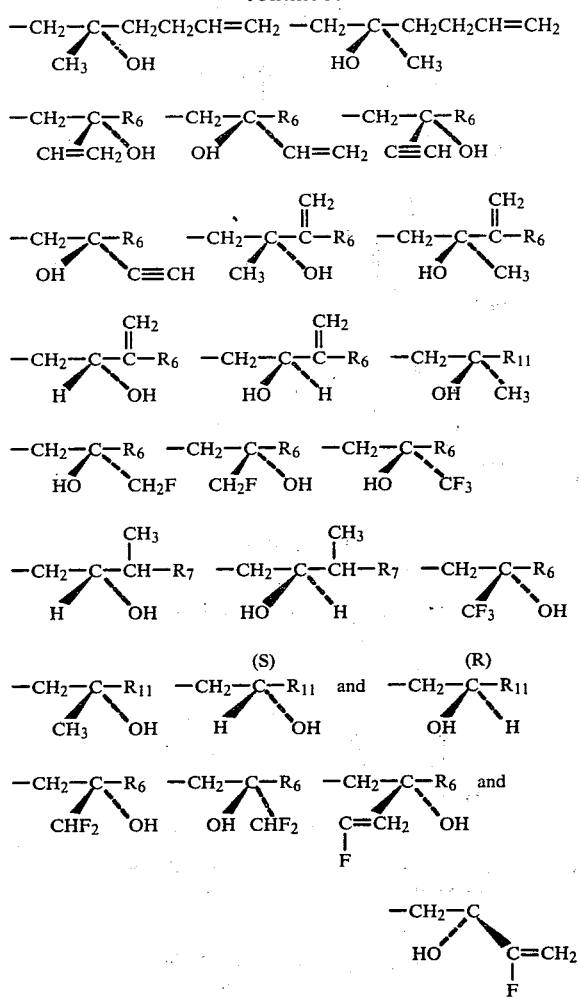

wherein R₆ is C₃ to C₅ alkyl, R₇ is C₂ to C₄ alkyl, R₁₀ is C₁ to C₄ alkyl and R₁₁ is C₃ to C₇ alkyl, the racemic mixtures thereof, the mirror images thereof and where R₂ is hydroxy, the pharmaceutically acceptable salts thereof.

2. The compounds according to claim 1 wherein X is cis—CH=CH—; R₂ is ethyl; and R₃ is as previously defined.

3. A racemic compound according to claim 2, dl-16-HYDROXY-1-CARBETHOXY-1,9-DIOXO-5-cis-13-trans-17-trans PROSTATRIENE.

4. A racemic compound according to claim 2, dl-16a-HYDROXY-1-CARBETHOXY-1,9-DIOXO-5-cis-13-trans-17-trans PROSTATRIENE.

5. A racemic compound according to claim 2, dl-16B-HYDROXY-1-CARBETHOXY-1,9-DIOXO-5-cis-13-trans-17-trans PROSTATRIENE.

6. A racemic compound according to claim 2, dl-16-HYDROXY-1-CARBETHOXY-1,9-DIOXO-16-METHYL-5-cis-13-trans-17-trans PROSTATRIENE.

7. A racemic compound according to claim 2, dl-16a-HYDROXY-1-CARBETHOXY-1,9-DIOXO-16-METHYL-5-cis-13-trans-17-trans PROSTATRIENE.

8. A racemic compound according to claim 2, dl-16B-HYDROXY-1-CARBETHOXY-1,9-DIOXO-16-METHYL-5-cis-13-trans-17-trans PROSTATRIENE.

9. A racemic compound according to claim 2, dl-16-HYDROXY-1-CARBETHOXY-1,9-DIOXO-5-cis-13-trans PROSTADIENE.

10. A racemic compound according to claim 2, dl-16a-HYDROXY-1-CARBETHOXY-1,9-DIOXO-5-cis-13-trans PROSTADIENE.

11. A racemic compound according to claim 2, dl-16B-HYDROXY-1-CARBETHOXY-1,9-DIOXO-5-cis-13-trans PROSTADIENE.

12. A racemic compound according to claim 2, dl-16-HYDROXY-1-CARBETHOXY-1,9-DIOXO-16-METHYL-5-cis-13-trans PROSTADIENE.

13. A racemic compound according to claim 2, dl-16a-HYDROXY-1-CARBETHOXY-1,9-DIOXO-16-METHYL-5-cis-13-trans PROSTADIENE.

14. A racemic compound according to claim 2, dl-16B-HYDROXY-1-CARBETHOXY-1,9-DIOXO-16-METHYL-5-cis-13-trans PROSTADIENE.

15. The racemic compound, dl-16-HYDROXY-1-CARBETHOXY-1,9-DIOXO-16-ETHYL-5-cis-13-trans PROSTADIENE.

16. The racemic compound, dl-16a-HYDROXY-1-CARBETHOXY-1,9-DIOXO-16-ETHYL-5-cis-13-trans PROSTADIENE.

17. The racemic compound, dl-16B-HYDROXY-1-CARBETHOXY-1,9-DIOXO-16-ETHYL-5-cis-13-trans PROSTADIENE.

18. A racemic compound according to claim 2, dl-16-HYDROXY-1-CARBETHOXY-1,9-DIOXO-17-METHYL-5-cis-13-trans PROSTADIENE.

19. A racemic compound according to claim 2, dl-16a-HYDROXY-1-CARBETHOXY-1,9-DIOXO-17-METHYL-5-cis-13-trans PROSTADIENE.

20. A racemic compound according to claim 2, dl-16B-HYDROXY-1-CARBETHOXY-1,9-DIOXO-17-METHYL-5-cis-13-trans PROSTADIENE.

21. A racemic compound according to claim 2, dl-16-HYDROXY-1-CARBETHOXY-1,9-DIOXO-17,17-DIMETHYL-5-cis-13-trans PROSTADIENE.

22. A racemic compound according to claim 2, dl-16a-HYDROXY-1-CARBETHOXY-1,9-DIOXO-17,17-DIMETHYL-5-cis-13-trans PROSTADIENE.

23. A racemic compound according to claim 2, dl-16B-HYDROXY-1-CARBETHOXY-1,9-DIOXO-17,17-DIMETHYL-5-cis-13-trans PROSTADIENE.

24. A racemic compound according to claim 2, dl-16-HYDROXY-1-CARBETHOXY-1,9-DIOXO-16-VINYL-5-cis-13-trans PROSTADIENE.

25. A racemic compound according to claim 2, dl-16a-HYDROXY-1-CARBETHOXY-1,9-DIOXO-16-VINYL-5-cis-13-trans PROSTADIENE.

26. A racemic compound according to claim 2, dl-16B-HYDROXY-1-CARBETHOXY-1,9-DIOXO-16-VINYL-5-cis-13-trans PROSTADIENE.

27. The racemic compound, dl-16-HYDROXY-1-CARBETHOXY-1,9-DIOXO-16-CYCLOPROPYL-5-cis-13-trans PROSTADIENE.

28. The racemic compound, dl-16a-HYDROXY-1-CARBETHOXY-1,9-DIOXO-16-CYCLOPROPYL-5-cis-13-trans PROSTADIENE.

29. The racemic compound, dl-16B-HYDROXY-1-CARBETHOXY-1,9-DIOXO-16-CYCLOPROPYL-5-cis-13-trans PROSTADIENE.

30. A racemic compound according to claim 2, dl-16-HYDROXY-1-CARBETHOXY-1,9-DIOXO-16-ETHYNYL-5-cis-13-trans PROSTADIENE.

31. A racemic compound according to claim 2, dl-16a-HYDROXY-1-CARBETHOXY-1,9-DIOXO-16-ETHYNYL-5-cis-13-trans PROSTADIENE.

32. A racemic compound according to claim 2, dl-16B-HYDROXY-1-CARBETHOXY-1,9-DIOXO-16-ETHYNYL-5-cis-13-trans PROSTADIENE.

33. A racemic compound according to claim 2, dl-16-HYDROXY-1-CARBETHOXY-1,9-DIOXO-17-METHYLENE-5-cis-13-trans PROSTADIENE.

34. A racemic compound according to claim 2 dl-16a-HYDROXY-1-CARBETHOXY-1,9-DIOXO-17-METHYLENE-5-cis-13-trans PROSTADIENE.

35. A racemic compound according to claim 2 dl-16B-HYDROXY-1-CARBETHOXY-1,9-DIOXO-17-METHYLENE-5-cis-13-trans PROSTADIENE.

36. A racemic compound according to claim 2 dl-16-HYDROXY-1-CARBETHOXY-1,9-DIOXO-16-METHYL-17-METHYLENE-5-cis-13-trans PROSTADIENE.

37. A racemic compound according to claim 2 dl-16-a-HYDROXY-1-CARBETHOXY-1,9-DIOXO-16-METHYL-17-METHYLENE-5-cis-13-trans PROSTADIENE.

38. A racemic compound according to claim 2 dl-16B-HYDROXY-1-CARBETHOXY-1,9-DIOXO-16-METHYL-17-METHYLENE-5-cis-13-trans PROSTADIENE.

39. The racemic compound dl-16-HYDROXY-1-CARBETHOXY-1,9-DIOXO-16-FORMYL-5-cis-13-trans PROSTADIENE.

40. The racemic compound, dl-16a-HYDROXY-1-CARBETHOXY-1,9-DIOXO-16-FORMYL-5-cis-13-trans PROSTADIENE.

41. The racemic compound, dl-16B-HYDROXY-1-CARBETHOXY-1,9-DIOXO-16-FORMYL-5-cis-13-trans PROSTADIENE.

42. A racemic compound according to claim 2, dl-16-HYDROXY-1-CARBETHOXY-1,9-DIOXO-16-FLUOROMETHYL-5-cis-13-trans PROSTADIENE.

43. A racemic compound according to claim 2, dl-16a-HYDROXY-1-CARBETHOXY-1,9-DIOXO-16-FLUOROMETHYL-5-cis-13-trans PROSTADIENE.

44. A racemic compound according to claim 2, dl-16B-HYDROXY-1-CARBETHOXY-1,9-DIOXO-16-FLUOROMETHYL-5-cis-13-trans PROSTADIENE.

45. A racemic compound according to claim 2, dl-16-HYDROXY-1-CARBETHOXY-1,9-DIOXO-16-DIFLUOROMETHYL-5-cis-13-trans PROSTADIENE.

46. A racemic compound according to claim 2, dl-16a-HYDROXY-1-CARBETHOXY-1,9-DIOXO-16-DIFLUOROMETHYL-5-cis-13-trans PROSTADIENE.

47. A racemic compound according to claim 2, dl-16B-HYDROXY-1-CARBETHOXY-1,9-DIOXO-16-DIFLUOROMETHYL-5-cis-13-trans PROSTADIENE.

48. A racemic compound according to claim 2, dl-16-HYDROXY-1-CARBETHOXY-1,9-DIOXO-16-TRIFLUOROMETHYL-5-cis-13-trans PROSTADIENE.

49. A racemic compound according to claim 2, dl-16a-HYDROXY-1-CARBETHOXY-1,9-DIOXO-16-TRIFLUOROMETHYL-5-cis-13-trans PROSTADIENE.

50. A racemic compound according to claim 2, dl-16B-HYDROXY-1-CARBETHOXY-1,9-DIOXO-16-TRIFLUOROMETHYL-5-cis-13-trans PROSTADIENE.

51. The racemic compound, dl-16-HYDROXY-1-CARBETHOXY-1,9-DIOXO-16-CHLOROMETHYL-5-cis-13-trans PROSTADIENE.

52. The racemic compound, dl-16a-HYDROXY-1-CARBETHOXY-1,9-DIOXO-16-CHLOROMETHYL-5-cis-13-trans PROSTADIENE.

53. The racemic compound, dl-16B-HYDROXY-1-CARBETHOXY-1,9-DIOXO-16-CHLOROMETHYL-5-cis-13-trans PROSTADIENE.

54. The racemic compound, dl-16-HYDROXY-1-CARBETHOXY-1,9-DIOXO-16-HYDROXYMETHYL-5-cis-13-trans PROSTADIENE.

55. The racemic compound, dl-16a-HYDROXY-1-CARBETHOXY-1,9-DIOXO-16-HYDROXYMETHYL-5-cis-13-trans PROSTADIENE.

56. The racemic compound, dl-16B-HYDROXY-1-CARBETHOXY-1,9-DIOXO-16-HYDROXYMETHYL-5-cis-13-trans PROSTADIENE.

57. The racemic compound, dl-16-HYDROXY-1-CARBETHOXY-1,9-DIOXO-16-METHYL-19-CHLORO-20-nor-5-cis-13-trans PROSTADIENE.

58. The racemic compound, dl-16a-HYDROXY-1-CARBETHOXY-1,9-DIOXO-16-METHYL-19-CHLORO-20-nor-5-cis-13-trans PROSTADIENE.

59. The racemic compound, dl-16B-HYDROXY-1-CARBETHOXY-1,9-DIOXO-16-METHYL-19-CHLORO-20-nor-5-cis-13-trans PROSTADIENE.

* * * * *